United States Patent
Yokoi et al.

(10) Patent No.: US 10,048,337 B2
(45) Date of Patent: Aug. 14, 2018

(54) IMAGE DIAGNOSIS APPARATUS AND POWER CONTROL METHOD OF AN IMAGE DIAGNOSIS APPARATUS

(71) Applicant: TOSHIBA MEDICAL SYSTEMS CORPORATION, Otawara-Shi (JP)

(72) Inventors: Motohisa Yokoi, Nasushiobara (JP); Motohiro Miura, Yaita (JP); Sho Kawajiri, Nasushiobara (JP); Kazuyuki Soejima, Nasushiobara (JP); Haruki Nakamura, Nasushiobara (JP); Naoki Imamura, Nasushiobara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1106 days.

(21) Appl. No.: 14/068,361

(22) Filed: Oct. 31, 2013

(65) Prior Publication Data
US 2014/0070812 A1 Mar. 13, 2014

Related U.S. Application Data

(63) Continuation of application No. PCT/JP2013/072717, filed on Aug. 26, 2013.

(30) Foreign Application Priority Data
Sep. 10, 2012 (JP) .................. 2012-198795

(51) Int. Cl.
*G01R 33/48* (2006.01)
*A61B 6/03* (2006.01)
(Continued)

(52) U.S. Cl.
CPC .............. *G01R 33/48* (2013.01); *A61B 6/03* (2013.01); *A61B 6/032* (2013.01); *A61B 6/56* (2013.01); *G01R 33/36* (2013.01)

(58) Field of Classification Search
CPC ............ G01R 33/4828; G01R 33/5611; G01R 33/565; G01R 33/3415; G01R 33/561;
(Continued)

(56) References Cited

U.S. PATENT DOCUMENTS

| 5,808,376 A | * | 9/1998 | Gordon .................. G01T 1/175 307/64 |
| 5,867,561 A | * | 2/1999 | Strasser .................. H05G 1/30 378/101 |

(Continued)

FOREIGN PATENT DOCUMENTS

| JP | 61-285518 | 12/1986 |
| JP | 07-255692 | 10/1995 |

(Continued)

OTHER PUBLICATIONS

Supplementary European Search Report dated May 12, 2016 in EP 13782929.7.

(Continued)

*Primary Examiner* — Dixomara Vargas
(74) *Attorney, Agent, or Firm* — Nixon & Vanderhye P.C.

(57) ABSTRACT

Image diagnosis apparatus (20) generates image data of an object by using external electric power, and includes a charge/discharge element and a charge/discharge control circuit. The charge/discharge element is charged with the external electric power and supplies part of the consumed power of the image diagnosis apparatus by discharging. The charge/discharge control circuit controls charge and discharge of the charge/discharge element in such a manner that the charge/discharge element discharges in a period during which the consumed power is larger than a predetermined power amount and the charge/discharge element is charged in a period during which the consumed power is smaller than the predetermined power amount.

18 Claims, 17 Drawing Sheets

(51) Int. Cl.
*G01R 33/36* (2006.01)
*A61B 6/00* (2006.01)

(58) Field of Classification Search
CPC ........ G01R 33/56; G01R 33/36; G01R 33/48;
G01R 33/54; G01R 33/4833; G01R
33/34046; G01R 33/34; G03G 15/0545;
G03G 15/054; G03G 13/22; H05G 1/10;
H05G 1/06; H05G 1/54; H05G 1/20;
H05G 1/24; H05G 1/34; A61B 6/03;
A61B 6/032; A61B 6/56
USPC .................. 378/32, 101, 103, 109, 111, 114
See application file for complete search history.

(56) References Cited

U.S. PATENT DOCUMENTS

| | | | | |
|---|---|---|---|---|
| 8,779,907 | B2* | 7/2014 | Liu | A61B 6/4405 |
| | | | | 340/384.1 |
| 9,472,973 | B2* | 10/2016 | Nakagawa | H02J 7/025 |
| 9,680,335 | B2* | 6/2017 | Kang | H02J 17/00 |
| 9,759,790 | B2* | 9/2017 | Kawajiri | A61B 5/055 |
| 9,823,676 | B2* | 11/2017 | Han | G05F 1/462 |
| 9,859,847 | B2* | 1/2018 | Paek | H03F 1/0227 |
| 2005/0028014 | A1* | 2/2005 | Allred | H02J 3/14 |
| | | | | 713/300 |
| 2010/0045113 | A1 | 2/2010 | Hishikawa et al. | |
| 2010/0172159 | A1 | 7/2010 | Kyono | |
| 2011/0103100 | A1* | 5/2011 | Hosotani | H01F 3/10 |
| | | | | 363/21.02 |
| 2011/0206272 | A1 | 8/2011 | Takaichi et al. | |
| 2011/0210739 | A1* | 9/2011 | Ham | G01R 33/28 |
| | | | | 324/318 |
| 2011/0249800 | A1 | 10/2011 | Sung et al. | |
| 2013/0147485 | A1 | 6/2013 | Yokoi | |
| 2013/0181638 | A1 | 7/2013 | Komatsu | |

FOREIGN PATENT DOCUMENTS

| | | |
|---|---|---|
| JP | 10-510135 | 9/1998 |
| JP | 11-99145 | 4/1999 |
| JP | 2003-52136 A | 2/2003 |
| JP | 2005-57997 | 3/2005 |
| JP | 2008-104760 | 5/2008 |
| JP | 2009-178375 | 8/2009 |
| JP | 2009-240526 | 10/2009 |
| JP | 2010-273782 A | 12/2010 |
| JP | 2011-176927 | 9/2011 |
| JP | 2012-040200 | 3/2012 |
| JP | 2012-050507 | 3/2012 |
| WO | WO 96/17260 | 6/1996 |

OTHER PUBLICATIONS

Supplementary European Search Report dated May 13, 2016 in EP 13782930.5.
English Translation of International Preliminary Report on Patentability dated Mar. 10, 2015 for Application No. PCT/JP2013/072718.
International Search Report for PCT/JP2013/072718, dated Sep. 17, 2013.
English Translation of International Preliminary Report on Patentability dated Mar. 10, 2015 for Application No. PCT/JP2013/072717.
International Search Report for PCT/JP2013/072717, dated Sep. 17, 2013.
JP Office Action dated May 8, 2018 in JP 2013-175330.

* cited by examiner

IMAGE DIAGNOSIS APPARATUS AND POWER CONTROL METHOD OF AN IMAGE DIAGNOSIS APPARATUS

CROSS-REFERENCE TO RELATED APPLICATIONS

This application is a Continuation Application of No. PCT/JP2013/72717, filed on Aug. 26, 2013, and the PCT application is based upon and claims the benefit of priority from Japanese Patent Application No. 2012-198795, filed on Sep. 10, 2012, the entire contents of which are incorporated herein by reference.

BACKGROUND OF THE INVENTION

1. Field of the Invention

Embodiments of the present invention relate to an image diagnosis apparatus and a power control method of an image diagnosis apparatus.

2. Description of the Related Art

MRI is an imaging method which magnetically excites nuclear spin of an object set in a static magnetic field with an RF pulse having the Larmor frequency and reconstructs an image on the basis of MR signals generated due to the excitation. The aforementioned MRI means magnetic resonance imaging, the RF pulse means a radio frequency pulse as an excitation pulse, and the MR signal means a nuclear magnetic resonance signal.

In recent years, high-speed imaging technology is promoted as represented by EPI (Echo Planar Imaging) and so on. When high-speed imaging such as EPI is performed, high output power is required in units of an imaging system such as an amplifier in an RF pulse transmitter and a gradient magnetic field power supply.

In an MRI apparatus, the electric power consumed in imaging is supplied from an external commercial power source. Thus, in order to enable the above high-speed imaging, i.e. in order to enable sufficient output, the maximum consumed power in the case of performance of the high-speed imaging, a power-supply facility of an MRI apparatus has been growing in size.

Incidentally, as conventional technology regarding power sources of a medical image generation system such as an MRI apparatus, the uninterruptible power source described in Patent Document 1 is known.

[Patent Document 1] Japanese Unexamined Patent Application Publication (Translation of PCT Application) No. 10-510135

If a power-supply facility of an MRI apparatus grows in size, it causes not only increase in facility expense but also restriction in site design. Concretely speaking, more restrictions are imposed on arranging of respective components of an MRI apparatus in an examination room and a computer room.

The above assignment is true of not only an MRI apparatus but also other image diagnosis apparatuses such as an X-ray computed tomography apparatus. Therefore, in image diagnosis apparatuses such as an MRI apparatus, a novel technology to downsize a power-supply facility without decreasing the maximum consumed power has been desired.

DETAILED DESCRIPTION

In order to downsize a power-supply facility without decreasing the maximum consumed power, the inventors have worked out a structure of a hybrid-type MRI apparatus. This MRI apparatus includes a charge/discharge element charged by electric power supplied from an external power source. This MRI apparatus consumes the accumulated electric power of the charge/discharge element, when the MRI apparatus runs short of electric power beyond the supplied electric power provided from the external power source during implementation term of imaging. Note that, the above charge/discharge element means a circuit element that can be repeatedly charged and discharged, like a capacitor and a secondary battery such as a lithium-ion rechargeable battery and a nickel hydride rechargeable battery.

Figure 1:
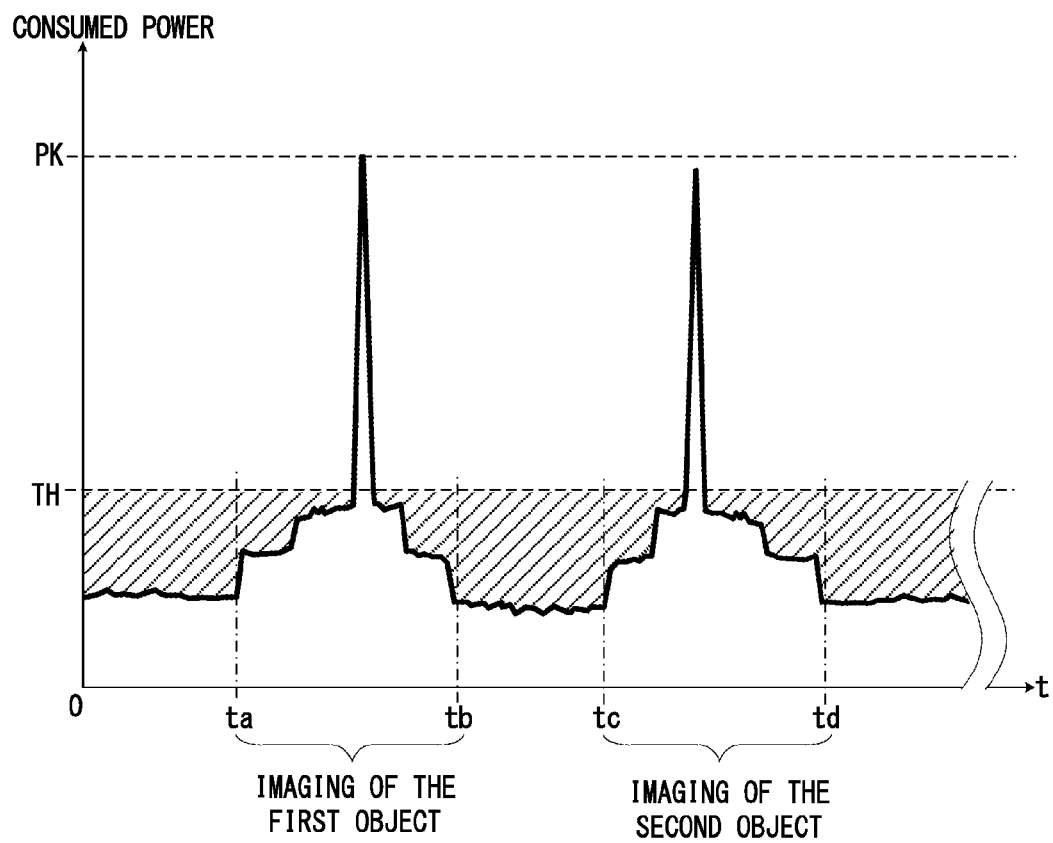
FIG. 1 is a schematic diagram showing a concept of an embodiment of a hybrid-type MRI apparatus by an example of the time variation of power consumption.

FIG. 1 is a schematic diagram showing a concept of an embodiment of a hybrid-type MRI apparatus by an example of the time variation of power consumption.

In FIG. 1, the vertical axis indicates the consumed power of the MRI apparatus, and the horizontal axis indicates elapsed time t. In addition, in FIG. 1, the period between time ta and time tb is an implementation term of an imaging sequence for the first object, and the period between time tc and time td is an implementation term of an imaging sequence for the second object.

During implementation term of an imaging sequence, there is a period in which consumed power shows a rapid rise in units of the imaging system such as an amplifier in a transmitter of RF pulses and a gradient magnetic field power supply.

In an MRI apparatus of conventional technology, a power-supply facility is large in size, because a power-supply facility which uses an external power source as source of electrical energy and is able to cover the maximum consumed power peak (PK) in terms of size is installed.

On the other hand, in MRI apparatuses of the following embodiments, the part using an external power source as source of electrical energy out of the power-supply facility is downsized to a degree sufficient to output consumed power of the threshold TH in FIG. 1 on a steady basis, for example. Then, during implementation term of an imaging sequence, the accumulated electric power of the charge/discharge element is supplied as apart of the consumed power when the electric power is deficient beyond the external electric power supplied from the external power source.

In this case, the charge/discharge element can be charged during a period in which the consumed power of the MRI apparatus is smaller than the threshold TH, in theory. That is, charging can be performed also during implementation term of an imaging sequence.

Hereinafter, examples of aspects which embodiments of the present invention can take will be explained per aspect.

(1) According to one embodiment of the present invention, the image diagnosis apparatus generates image data of an object by consuming external electric power supplied from an external power source, and includes a charge/discharge element and a charge/discharge control circuit.

The charge/discharge element is charged with the external electric power and supplies a part of consumed power of the image diagnosis apparatus by discharging.

The charge/discharge control circuit controls discharge and charge of the charge/discharge element in such a manner that the charge/discharge element discharges in a period during which consumed power is larger than a predetermined power amount, and the charge/discharge element is charged in a period during which the consumed power is smaller than the predetermined power amount.

(2) According to one embodiment of the present invention, a power control method of an image diagnosis apparatus is a power control method for an image diagnosis apparatus that generates image data of an object by consuming external electric power supplied from an external power source. In this power control method, discharge and charge of a charge/discharge element of the image diagnosis apparatus is controlled in such a manner that a part of consumed power of the image diagnosis apparatus is supplied from the charge/discharge element in a period during which the consumed power is larger than a predetermined power amount and the charge/discharge element is charged with the external electric power in a period during which the consumed power is smaller than the predetermined power amount.

Some examples of embodiments of an image diagnosis apparatus and a power control method of an image diagnosis apparatus to which the above innovative technology are applied will be described with reference to the accompanying drawings. Note that cases of MRI apparatuses will be explained as an example of an image diagnosis apparatus in the first embodiment to the fourth embodiment. In addition, the same reference numbers are given for identical components in each figure, and overlapping explanation is abbreviated.

The First Embodiment

Figure 2:
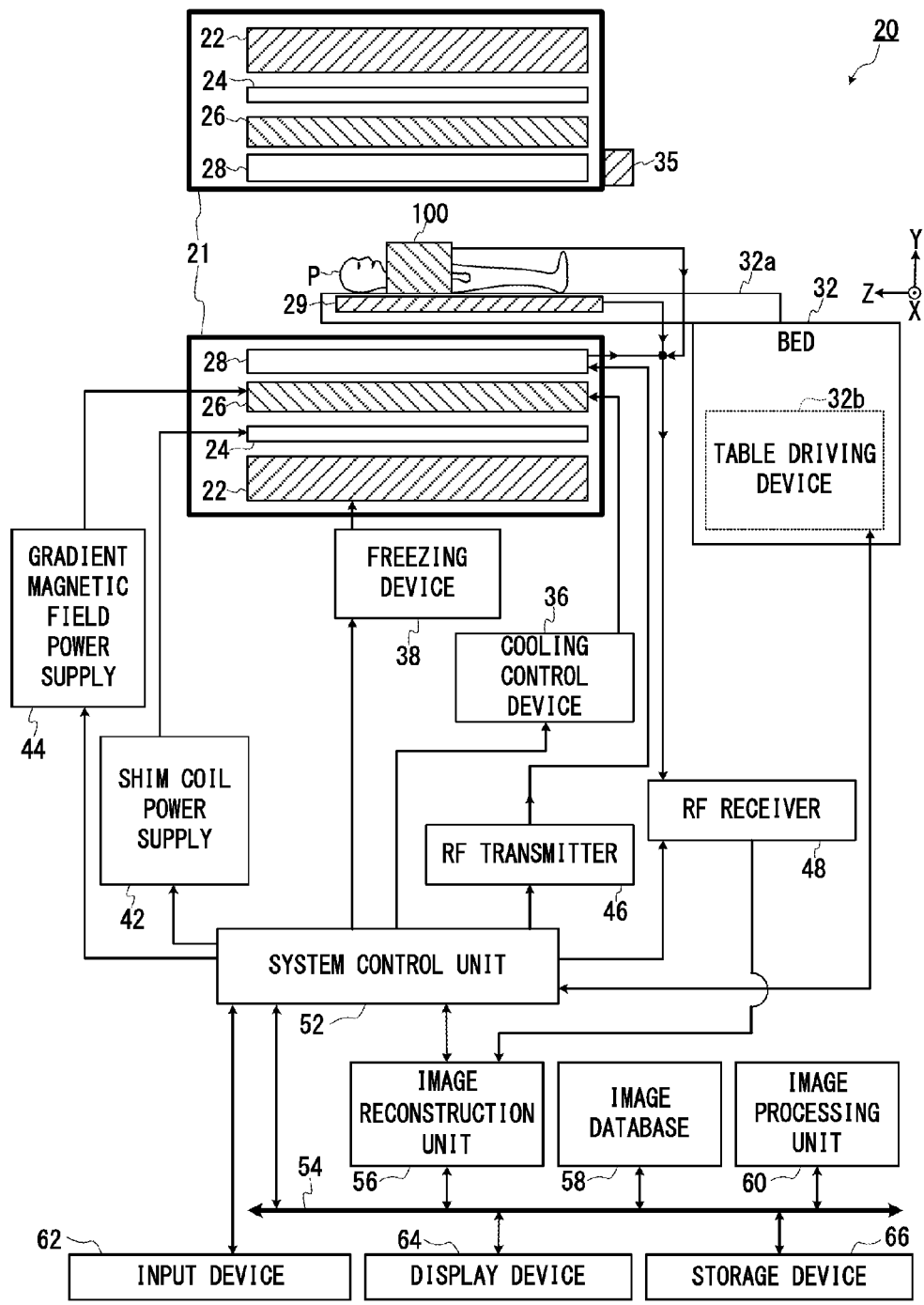
FIG. 2 is a functional block diagram mainly showing the structure of the imaging system of the MRI apparatus of the first embodiment.

FIG. 2 is a functional block diagram mainly showing the structure of the imaging system of the MRI apparatus 20 of the first embodiment. As shown in FIG. 2, the MRI apparatus 20 includes a gantry 21, a bed 32 and a projector 35.

The bed 32 includes a table 32a and a table driving device 32b which moves the table 32a in a predetermined direction. The table 32a is movably supported by the bed 32. An object P is loaded on the table 32a.

The projector 35 is disposed on the portion of the opening of the gantry 21, and irradiates light for positioning towards the table 32a.

In addition, the MRI apparatus 20 includes a static magnetic field magnet 22, a shim coil 24, a gradient magnetic field coil 26, a transmission RF coil 28, a reception RF coil 29, a shim coil power supply 42, a gradient magnetic field power supply 44, an RF transmitter 46, an RF receiver 48 and a system control unit 52, as a data collecting system.

In addition, the MRI apparatus 20 includes a system bus 54, an image reconstruction unit 56, an image database 58 and an image processing unit 60, as a data processing system.

The imaging system consisting of the above data collecting system and the data processing system performs MRI by consuming the external electric power supplied from an external electric power source, and thereby image data of the object P are generated.

Moreover, the MRI apparatus 20 includes an input device 62, a display device 64 and a storage device 66.

The static magnetic field magnet 22, the shim coil 24, the gradient magnetic field coil 26 and the transmission RF coil 28 are disposed in the gantry 21.

The static magnetic field magnet 22 and the shim coil 24 are, for example, cylinder-shaped, and the shim coil 24 is coaxially arranged inside the static magnetic field magnet 22.

As an example here, an apparatus coordinate system, whose X axis, a Y axis and a Z axis are perpendicular to each other, is defined as follows. Firstly, the Z axis direction is defined as the direction of an axis of the static magnetic field magnet 22. In addition, it is assumed that the vertical direction is the same as the Y axis direction. Moreover, the table 32a is disposed in such a position that the direction of the normal line of its loading plane is the same as the Y axis direction.

The static magnetic field magnet 22 forms a static magnetic field magnet in an imaging space in the gantry 21.

The shim coil 24 is electrically connected to the shim coil power supply 42 and uniforms the static magnetic field with the electric current supplied from the shim coil power supply 42.

Note that, if the static magnetic field formed by the static magnetic field magnet 22 can be kept sufficiently uniform (after inserting an object into the imaging space), the shim coil 24 and the shim coil power supply 42 may be omitted. Thus, in the later-described FIG. 14, the shim coil power supply 42 is not an essential component.

The gradient magnetic field coil 26 is, for example, arranged inside the static magnetic field magnet 22 in the form of a cylinder. The gradient magnetic field coil 26 generates a gradient magnetic field Gx in the X axis direction, a gradient magnetic field Gy in the Y axis direction and a gradient magnetic field Gz in the Z axis direction in the imaging region, by using electric currents supplied from the gradient magnetic field power supply 44.

That is, directions of a gradient magnetic field Gss in a slice selection direction, a gradient magnetic field Gpe in a phase encoding direction and a gradient magnetic field Gro in a readout (frequency encoding) direction can be arbitrarily set as logical axes, by combining the gradient magnetic fields Gx, Gy and Gz in the three axes of the apparatus coordinate system.

Note that, the above imaging region means, for example, a region set as a part of the imaging space and is a range of acquisition of MR signals used to generate one image or one set of image. The one set of images means, for example, a plurality of images when MR signals of the plurality of images are acquired in a lump in one pulse sequence such as multi-slice imaging. The imaging region is defined three-dimensionally in the apparatus coordinate system, for example.

The RF transmitter 46 generates RF pulses (RF pulse electric current) of the Larmor frequency for causing nuclear magnetic resonance in accordance with control information inputted from the system control unit 52, and transmits the generated RF pulses to the transmission RF coil 28. The transmission RF coil 28 receives the RF pulses from the RF transmitter 46, and transmits the RF pulses to the object P.

Note that, the transmission RF coil 28 includes a whole body coil (not shown) which is built-in the gantry 21 and used for both transmission of the RF pulses and detection of MR signals.

A reception RF coil 29 is disposed inside the table 32a, or on the table 32a. The reception RF coil 29 detects MR signals generated due to excited nuclear spin inside the object P by the RF pulses, and transmits the detected MR signals to the RF receiver 48.

Note that, as an example in FIG. 2, a wearable type RF coil device 100 for local detection of the MR signals is set on the object P.

The RF receiver 48 performs predetermined signal processing on the MR signals detected by these reception RF coil 29 and the wearable type RF coil device 100 if necessary, and then performs A/D (analog to digital) conversion on them. Thereby, the RF receiver 48 generates raw data which are complex number data of digitized MR signals. The RF receiver 48 inputs the generated raw data of MR signals to the image reconstruction unit 56.

The image reconstruction unit 56 arranges the raw data of MR signals inputted from the RF receiver 48, as k-space data. The k-space means a frequency space (Fourier space). The image reconstruction unit 56 generates image data of the object P by performing image reconstruction processing including such as two-dimensional Fourier transformation on the k-space data. The image reconstruction unit 56 stores the generated image data in the image database 58.

The image processing unit 60 takes in the image data from the image database 58, performs predetermined image processing on them, and stores the image data after the image processing in the storage device 66 as display image data.

The storage device 66 stores the display image data after adding accompanying information such as the imaging conditions used for generating the display image data and information of the object P (patient information) to the display image data.

The display device 64 displays a screen for setting the conditions of the imaging sequence and images indicated by the generated image data in accordance with control of the system control unit 52.

The system control unit 52 performs system control of the entirety of the MRI apparatus 20 in imaging operation and image display after imaging operation via interconnection lines such as the system bus 54.

In order to achieve that, the system control unit 52 stores control information needed in order to make the gradient magnetic field power supply 44, the RF transmitter 46 and the RF receiver 48 drive. The aforementioned control information includes, for example, sequence information describing operation control information such as intensity, application period and application timing of the pulse electric currents which should be applied to the gradient magnetic field power supply 44.

The system control unit 52 generates the gradient magnetic fields Gx, Gy and Gz and RF pulses by driving the gradient magnetic field power supply 44, the RF transmitter 46 and the RF receiver 48 according to a set imaging sequence.

In addition, the system control unit 52 can move up and down the table 32a in the Y axis direction by controlling the table driving device 32b, when the table 32a is outside the gantry 21.

In addition, the system control unit 52 makes the table 32a move in the Z axis direction so as to move into and out of the imaging space in the gantry 21, by controlling the table driving device 32b.

The system control unit 52 locates the imaging part of the object P on the table 32a near to the center of the magnetic field in the imaging space, by controlling the position of the table 32a in the Z axis direction.

In addition, the system control unit 52 functions as a condition setting unit of imaging sequences. That is, the system control unit 52 sets all the conditions of the imaging sequences on the basis of some of the conditions of the imaging sequences and information on the object P inputted to the input device 62 by a user. In order to achieve that, the system control unit 52 makes the display device 64 display screen information for setting conditions of an imaging sequence.

The input device 62 provides a user with a function of setting conditions of imaging sequences and image processing conditions.

The aforementioned term conditions of imaging sequences refers to under what condition an RF pulse or the like is transmitted in what type of pulse sequence, and under what condition MR signals are acquired from an object as a main scan, for example.

As an example of conditions of an imaging sequence, for example, there are the imaging region as positional information in the imaging space, an imaging part, the type of the pulse sequence such as parallel imaging, the type of RF coil devices used for imaging, the number of slices, an interval between respective slices.

The above imaging part means, for example, a region of the object P to be imaged as an imaging region, such as a head, a chest and an abdomen.

The aforementioned main scan is a scan for imaging an intended diagnosis image such as a proton density weighted image, and it does not include a scan for acquiring MR signals for a scout image or a calibration scan.

A scan is an operation of acquiring MR signals, and it does not include image reconstruction processing.

The calibration scan is, for example, a scan for determining unconfirmed elements of conditions of the main scan, conditions and data used for image reconstruction processing and so on, and it is performed separately from the main scan. Out of calibration scans, a prescan is a scan which is performed before the main scan (for example, at the timing of Step S1 in the later-described FIG. 8).

The MRI apparatus 20A further includes a cooling control device 36 and a freezing device 38.

The cooling control device 36 cools down the gradient magnetic field coil 26 and the transmission RF coil 28 inside the gantry 21 by circulating a cooling medium in cooling pipes (not shown) in the gantry 21.

The freezing device 38 cools down the static magnetic field magnet 22 on a steady basis by using, for example, liquid helium.

Figure 3:
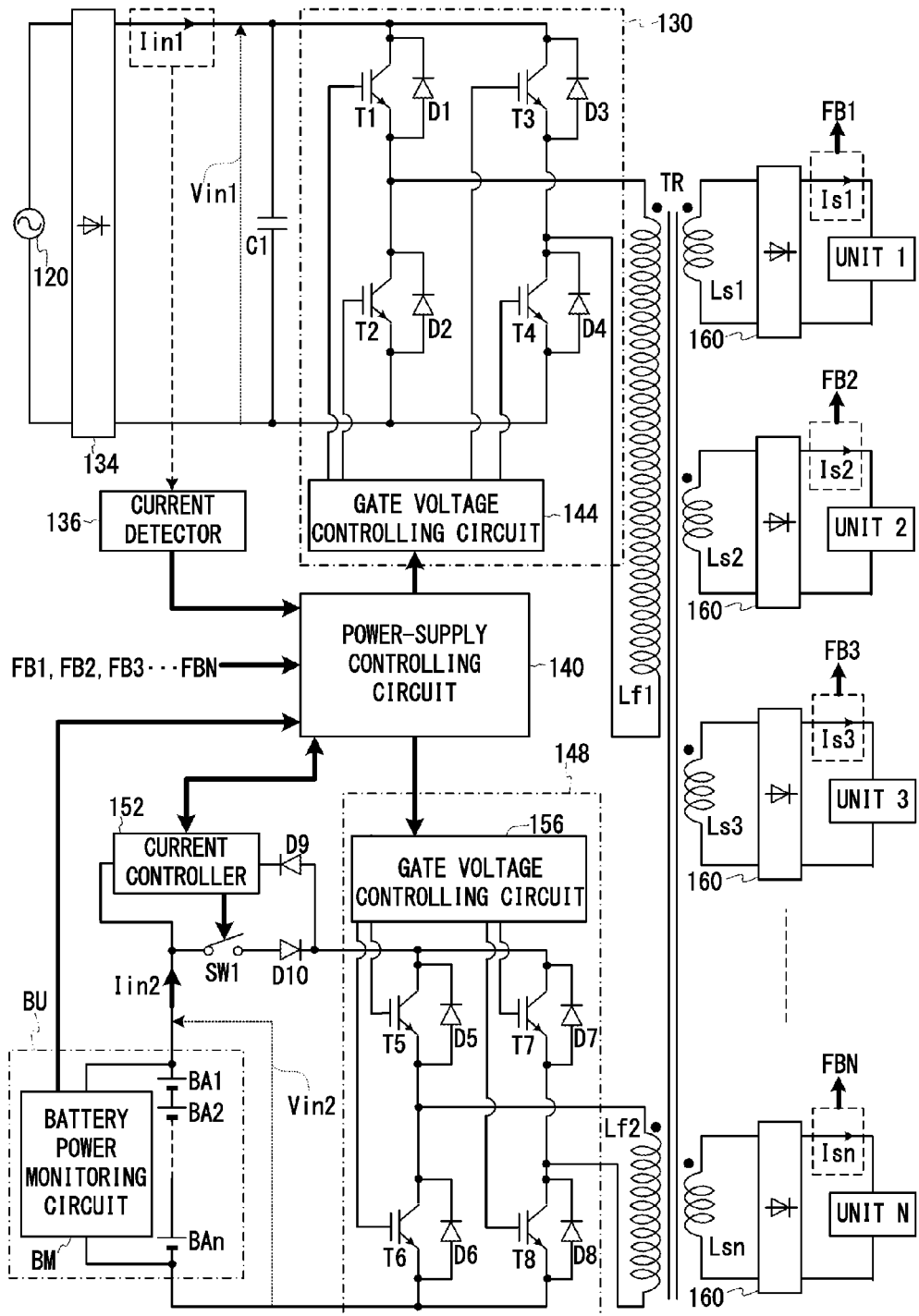
FIG. 3 is a schematic circuit diagram of the electric power supply system of the MRI apparatus of the first embodiment.

FIG. 3 is a schematic circuit diagram of the electric power supply system of the MRI apparatus 20 of the first embodiment.

As shown in FIG. 3, the transformer TR of the MRI apparatus 20 includes the first primary winding Lf1, the second primary winding Lf2 and n pieces of the secondary windings which are magnetically coupled to each other. The n pieces of the secondary windings are the first secondary winding Ls1, the second secondary winding Ls2, the third secondary winding Ls3, . . . and the n-th secondary winding Lsn.

The power supply system of the MRI apparatus 20 is a forward type AC/DC converter (alternate current/direct current converter) which transmits the alternating external electric power supplied from the external power source 120 to the secondary side as direct-current electric power. Thus, the magnetic connection between the first primary winding Lf1 and each of the secondary windings Ls1 to Lsn is homopolarity, and the magnetic connection between the second primary winding Lf2 and each of the secondary windings Ls1 to Lsn is homopolarity. In addition, the magnetic connection between the first primary winding Lf1 and the second primary winding Lf2 is homopolarity.

However, the above is only an example. The magnetic connection between the first and second primary windings Lf1, Lf2 and each of the secondary windings Ls1 to Lsn may be reversed polarity. That is, it may be configured as a power circuit of a flyback converter. In addition, it may be interpreted as a DC/DC converter, because it converts the external electric power from the external power source 120 into direct current on the primary side and then supply direct-current power to each unit of the secondary side.

In the following, the circuit structure will be explained in the order of the primary side, the secondary side of the transformer TR.

The power supply system of the MRI apparatus 20 includes the first switching circuit 130 connected in parallel to the first primary winding Lf1, a smoothing capacitor C1 and a rectifier 134 connected in parallel to the first switching circuit 130.

In addition, the power supply system of the MRI apparatus 20 further includes a current detector 136 and a power-supply controlling circuit 140 as a control circuit of the first switching circuit 130.

The rectifier 134 converts the alternating external electric power supplied from the external power source 120 into direct current, and outputs direct-current electricity. The external power source 120 is, for example, a commercial power source. Hereinafter, the output voltage (and its value) of the rectifier 134 is referred to as the primary side voltage Vin1, and the output current (and its value) of the rectifier 134 is referred to as the primary side current Iin1. The current detector 136 detects the primary side current Iin1, and inputs this to the power-supply controlling circuit 140.

The first switching circuit 130 is a full-bridge circuit. The first switching circuit 130 includes four transistors T1, T2, T3 and T4 as switching elements, and the gate voltage controlling circuit 144 that controls the gate voltages of them.

Each of the transistors T1, T2, T3 and T4 are, for example, IGBT (Insulated Gate Bipolar Transistor). As shown in FIG. 3, the transistors T1, T2, T3 and T4 respectively include parasitic diodes D1, D2, D3 and D4 whose forward directions is the direction from the emitter to the collector.

Note that, the transistors T1, T2, T3 and T4 may be not IGBT but other switching elements such as power MOS (Metal-Oxide-Silicon) transistors.

The power-supply controlling circuit 140 inputs control information such as an on-span, an off-span and a dead time (short-circuit protection period) to the gate voltage controlling circuit 144, in accordance with the later-described feedback signals FB1, FB2, FB3, . . . FBN inputted from the secondary side and the conditions of the imaging sequence. The gate voltage controlling circuit 144 outputs each of the gate voltages of the transistors T1, T2, T3 and T4 in accordance with this control information.

The transistors T1, T2, T3 and T4 switch to on (conduction state) or off (nonconductive state), in accordance with the gate voltages inputted from the gate voltage controlling circuit 144. Thus, the control of the output voltage of the secondary side is a duty ratio control by the power-supply controlling circuit 140 and the first switching circuit 130.

Next, the second primary winding Lf2 side will be explained. The power supply system of the MRI apparatus 20 includes the second switching circuit 148 connected in parallel to the second primary winding Lf2, a battery unit BU, a switch SW1, diodes D9 and D10, and a current controller 152.

The second switching circuit 148 is a full-bridge circuit. The second switching circuit 148 includes four transistors T5, T6, T7 and T8 as switching elements and the gate voltage controlling circuit 156 that controls the gate voltages of them.

Each of the transistors T5, T6, T7 and T8 is, for example, IGBT. The transistors T5, T6, T7 and T8 respectively include regeneration diodes D5, D6, D7 and D8 which regenerate energy from the reverse current in the direction from the emitter side to the collector side.

Note that, the transistor T5 to T8 may be not IGBT but other switching elements such as power MOS transistors.

The power-supply controlling circuit 140 inputs control information such as an on-span, an off-span and a dead time to the gate voltage controlling circuit 156, in accordance with the feedback signals FB1 to FBN and the conditions of the imaging sequence. The gate voltage controlling circuit 156 outputs each of the gate voltages of the transistors T5 to T8 in accordance with this control information.

The transistors T5 to T8 switch to on (conduction state) or off (nonconductive state) in accordance with the gate voltages inputted from the gate voltage controlling circuit 156.

The battery unit BU includes a plurality of series-connected rechargeable batteries BA1, BA2, . . . , BAn, and a battery power monitoring circuit BM. As an example here, the rechargeable batteries BA1 to BAn are lithium ion rechargeable batteries, but these may be other charge/discharge elements. The battery power monitoring circuit BM detects the charging voltage Vin2 of the battery unit BU which is the total voltage of the rechargeable batteries BA1 to BAn, and inputs the amplitude (value) of the charging voltage Vin2 to the power-supply controlling circuit 140.

The current controller 152 switches charge and discharge states of the battery unit BU in accordance with the control signal inputted from the power-supply controlling circuit 140. More specifically, the current controller 152 switches the battery unit BU to a discharging state, by turning on the switch SW1 and turning the pathway between the cathode side of the diode D9 and the positive terminal side of the battery unit BU into a nonconductive state.

In addition, the current controller 152 switches the battery unit BU to a standby state (a state in which charge or discharge of the battery unit BU is not performed), by turning off the switch SW1 and turning the pathway between the cathode side of the diode D9 and the positive terminal side of the battery unit BU into a nonconductive state.

In addition, the current controller 152 switches the battery unit BU to a charging state, by turning off the switch SW1 and turning the pathway between the cathode side of the diode D9 and the positive terminal side of the battery unit BU into a conductive state. At this time, the current controller 152 protects the battery unit BU by restricting the amount of the charging current flowing from the diode D9 into the positive terminal side of the battery unit BU.

Note that, the current (and its value) outputted from the positive terminal side of the battery unit BU is referred to as the discharging current Iin2.

Next, the secondary side will be explained. In the secondary side, the rectifiers 160 are respectively connected in parallel to the secondary windings Ls1 to Lsn. Each of the rectifiers 160 supplies the secondary side currents of direct-current to each of the units 1, 2, 3, . . . N, by rectifying the induced currents respectively generated in the secondary windings Ls1 to Lsn.

The units 1 to N are the respective components of the MRI apparatus 20 which consume electric power, and they are the table driving device 32b, the cooling control device 36, the freezing device 38, the shim coil power supply 42, the gradient magnetic field power supply 44, the RF transmitter 46, the RF receiver 48, the system control unit 52 and the computer system. The computer system is the image reconstruction unit 56, the image database 58, the image processing unit 60, the input device 62, the display device 64, the storage device 66 and so on (see FIG. 2).

Thus, the unit 1 is, for example, the gradient magnetic field power supply 44 which has the maximum consumed power and the maximum variation in the consumed power during implementation term of an imaging sequence. The unit 2 is, for example, the RF transmitter 46. The unit 3 is, for example, the freezing device 38. The unit N is, for example, the computer system. As to the unit of the computer system, an uninterruptible power source (not shown) may be arranged in the rear stage of the rectifier 160 in order to prevent data missing, for example.

These respective units 1 to N generate the feedback signals FB1 to FBN, and input these feedback signals FB1 to FBN into the power-supply controlling circuit 140, respectively.

Note that, in each component of the MRI apparatus 20, components which do not vary a lot in the consumed power and thus do not have a merit of receiving power from the battery unit BU may be excluded from the secondary side in FIG. 3 and be supplied with electric power by another method. The other method is, for example, to make the external power source 120 directly provide it with electric power (see later-described unit 1 of FIG. 15 and FIG. 16).

Next, the setting method of a winding number of each of the first primary winding Lf1, the second primary winding Lf2 and the secondary windings will be explained. The consumed voltage (and its value) of the unit N is defined as VoutN, the winding number of the first primary winding Lf1 is defined as Tf1, the winding number of the secondary winding of the unit N is defined as TsN, the margin ration of the power supply system of the MRI apparatus 20 is defined as Kp.

Because the voltage depression amount in the transistors T1 and T4 (or the transistors T2, T3) in the conductive state is small as compared with the primary side voltage Vin1, it is approximated that the voltage of the first primary winding Lf1 is equal to the primary side voltage Vin1. Then, the winding numbers are set so as to satisfy the next equation (the same applies to other units 1, 2, 3 and so on in the secondary side).

$$VoutN/TsN = Kp \times (Vin1/Tf1) \qquad (1)$$

In the equation (1), the margin ratio Kp is a positive value smaller than 1, and is, for example, a value approximately 0.5 to 0.9. In addition, in the equation (1), the primary side voltage Vin1 and the consumed voltage VoutN of the unit N are evaluated in absolute values, regardless of a positive sign or a negative sign (the same applies to the later-described equation (3) to (6)).

Next, consider an electrifiable condition. In time of charging, all the transistors T5 to T8 of the second switching circuit 148 are turned off, and a charging current flows into the battery unit BU via the regeneration diodes D5 and D8 (or the regeneration diodes D6 and D7).

At this time, the battery unit BU cannot be charged up to the charging voltage at completion of charging, if the voltage obtained by subtracting 'the voltage drop amount in the current controller 152, the diode D9 and the regeneration diodes D5 and D8' from 'the voltage Vf2 induced in the second primary winding Lf2' is not larger than the maximum value of the charging voltage Vin2 (the voltage Vin2m at completion of charging).

That is, the winding numbers are set in such a manner that the voltage obtained by subtracting 'the voltage drop amount in the current controller 152, the diode D9 and the regeneration diodes D5 and D8' from 'the voltage Vf2 induced in the second primary winding Lf2 in time of flowing an excitation current in the first primary winding Lf1' is larger than the voltage Vin2m at completion of charging. By approximating that the voltage drop amount in the current controller 152, the diode D9 and the regeneration diodes D5 and D8 is negligibly-small as compared with the voltage Vf2 of the second primary winding Lf2, the winding numbers are set so as to satisfy the next equation.

$$Vin2m < Vf2 \qquad (2)$$

Note that, in the equation (2), the charging voltage Vin2m and the voltage Vf2 of the second primary winding Lf2 are evaluated in absolute values, regardless of a positive sign or a negative sign (the same applies to the later-described equation (3) to (6)). Here, as to the voltage Vf2 of the second primary winding Lf2, the next equation is established.

$$Vf2/Tf2 = Vin1/Tf1 \qquad (3)$$

By dividing both sides of the equation (2) by Tf2 and then substituting it into the equation (3), the electrifiable condition is to set the winding numbers so as to satisfy the next following equation.

$$Vin2m/Tf2 < Vin1/Tf1 \quad (4)$$

Moreover, considering the voltage VoutN induced in the N-the secondary winding Lsn (the consumed voltage in the unit N), there is a possibility that a dead time of turning off all the transistors T1 to T8 disappears in a half cycle of switching in the case of satisfying the following equation.

$$VoutN/TsN = Vin2m/Tf2 \quad (5)$$

That is, it is preferable that the right side is larger than left side in the equation (5). By combining this point with the electrifiable condition of the equation (4), the winding numbers are set so as to satisfy the following equation (the same applies to other unit on the secondary side).

$$VoutN/Tsn < Vin2m/Tf2 < Vin1/Tf1 \quad (6)$$

Here, the required supply voltage differs per each unit 1 to N on the secondary side. A large voltage should be supplied, if the consumed power is relatively large as compared with other units like the gradient magnetic field power supply 44.

Thus, the winding number of each of the secondary windings Ls1 to Lsn is properly adjusted for each winding number of the first primary winding Lf1 and the second primary winding Lf2, in such a manner that the equations (1) to (6) are satisfied and each voltage supplied to each of the units 1 to N on the secondary side becomes an intended voltage proper for the respective units 1 to N. Therefore, for example, in FIG. 3, if the unit 1 is the gradient magnetic field power supply 44 whose consumed power is large, the winding number of the unit 1 on the secondary windings Ls1 is larger than each winding number of the other secondary windings Ls2 to Lsn.

Next, the circuit operation of the power supply system of the MRI apparatus 20 will be explained.

As shown in FIG. 3, the power supply system of the MRI apparatus 20 performs duty ratio control by the first switching circuit 130 and the second switching circuit 148.

Thus, when a feedback signal (such as FB1) indicative of increase of the consumed power on the secondary side is inputted to the power-supply controlling circuit 140, the ratio of on-span in one cycle of the transistors T1 to T4 increases and each of the induced currents in the respective secondary windings increases. However, there is an upper limit Onmax in the ratio of on-span in one cycle of the transistors T1 to T4, and this upper limit corresponds to, for example, a case of consuming the maximum value of the external electric power supplied from the external power source 120.

When the consumed power on the secondary side becomes insufficient beyond the maximum available electric power from the external power source 120 (the maximum value of the external electric power), this shortfall is covered with the discharging current from the battery unit BU. When the battery unit BU discharges, the ratio of on-span in one cycle of the transistors T1 to T4 is kept at the upper limit Onmax.

Here, the circuit operation of the power supply system of the MRI apparatus 20 is classified into three, on the basis of the discharge and charge states of the battery unit BU. In the following explanation, the case where discharge or charge of the battery unit BU is not performed is referred to as a standby mode, the case of discharging is referred to as a discharging mode, and the case of charging is referred to as a charging mode. The power-supply controlling circuit 140 switches the mode of the power supply system of the MRI apparatus 20 from one of the standby mode, the discharging mode and the charging mode to another of them. In the following, they are explained in the order of the standby mode, the discharging mode, and the charging mode, with reference to FIG. 4, FIG. 5 and FIG. 6.

Figure 4:
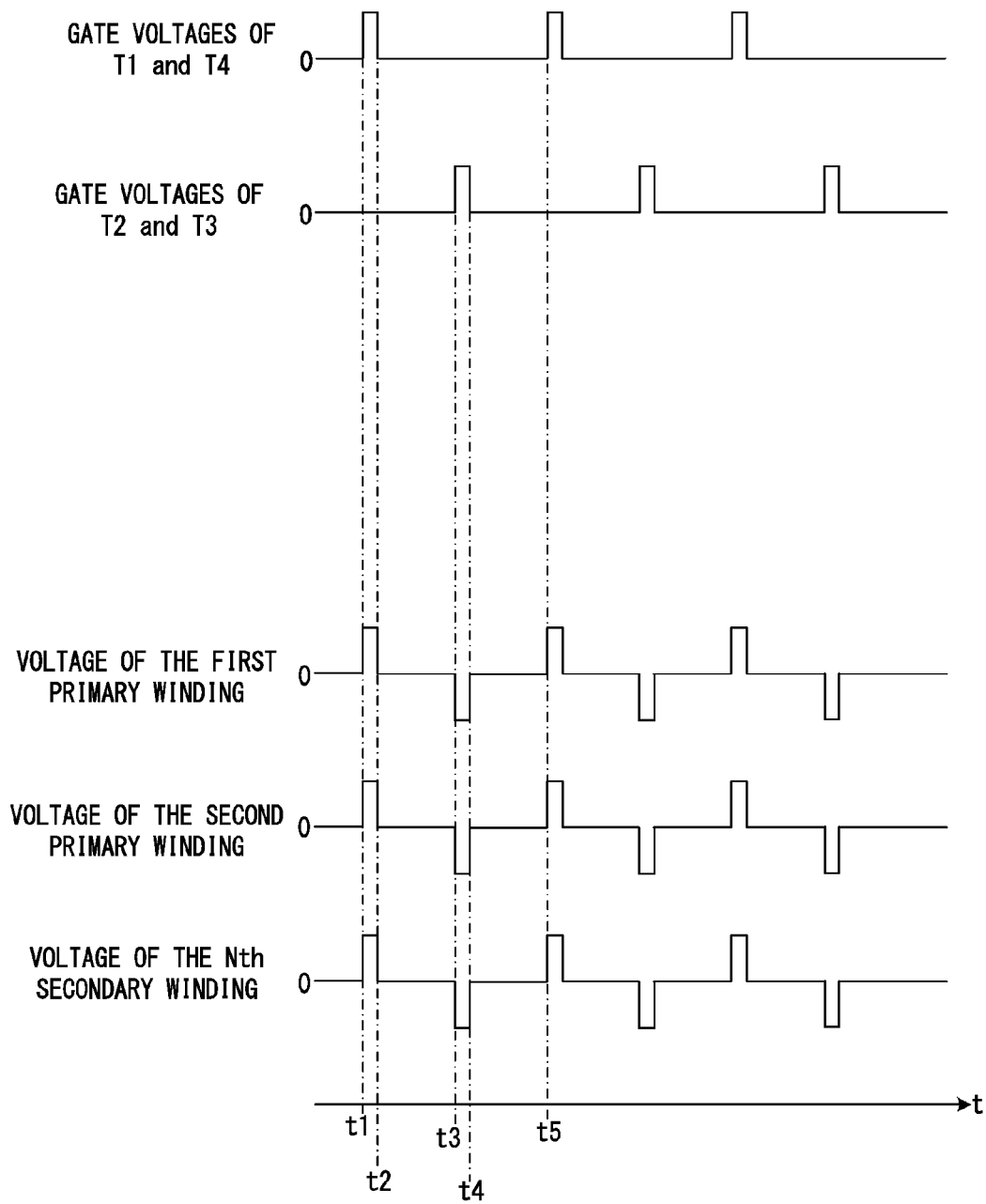
FIG. 4 is a schematic diagram showing an example of the voltage waveforms of the respective components of the electric power supply system of the MRI apparatus of the first embodiment, when discharge and charge of the battery unit are not performed.

FIG. 4 is a schematic diagram showing an example of the voltage waveforms of the respective components of the electric power supply system of the MRI apparatus 20, in the standby mode (when discharge or charge of the battery unit BU is not performed). In FIG. 4, each horizontal axis indicates elapsed time t.

In FIG. 4, time variations are indicated for the gate voltages of the transistors T1 and T4, the gate voltages of the transistors T2 and T3, the voltage of the first primary winding Lf1, the voltage of the second primary winding Lf2, and the voltage of the N-th secondary winding Lsn, from top to bottom. In the example of FIG. 4, one cycle of switching is the period between time t1 and time t5, the period between time t1 and time t3 is a half cycle of switching, and the period between time t3 and time t5 is a half cycle of switching.

Note that, the case where discharge or charge of the battery unit BU is not performed means, for example, a case of satisfying the following two conditions.

The first condition is that the consumed power on the secondary side is not more than the maximum value of the external electric power which is transmittable to the secondary side via the first primary winding Lf1. This is because discharge of the battery unit BU is not necessary in this case.

The second condition is that charging of the battery unit BU is not necessary. The case where charging of the battery unit BU is not necessary means, for example, a case where the battery unit BU is fully charged, more specifically, a case where its charging voltage Vin2 is the maximum value.

When discharge or charge of the battery unit BU is not performed, the gate voltage controlling circuit 156 of the second switching circuit 148 keeps each of the transistors T5 to T8 at off-state. In this case, the current controller 152 blocks out inflow of the charging current into the battery unit BU via the regeneration diodes D5 to D8 by electrically blocking out the route between the diode D9 the battery unit BU, and turns off the switch SW1 in addition to that. By keeping the above condition, the battery unit BU is isolated in terms of a circuit, and discharge and charge are prevented.

In the following, the circuit operation of the standby mode (a case where discharge or charge is not performed) will be explained according to time t1 to time t5 shown in FIG. 4.

Firstly, at time t1, the gate voltage controlling circuit 14 of the first switching circuit 130 switches the gate voltages of the transistors T1 and T4 from off-level to on-level in accordance with the control information inputted from the power-supply controlling circuit 140. Thereby, the primary side current Iin1 of direct-current outputted from the positive side output terminal of the rectifier 134 flows as the excitation current in the order of the transistor T1 first, then the first primary winding Lf1 then the transistor T4, and then returns to the negative side output terminal of the rectifier 134.

Here, in the first primary winding Lf1, it is assumed that the transistor T1 side (the top side of paper of FIG. 3) is assumed to be the high voltage side, and the transistor T4 side (the bottom side of paper of FIG. 3) is assumed to be the low voltage side.

In addition, in the second primary winding Lf2, the transistor T5 side (the top side of paper of FIG. 3) is assumed to be the high voltage side, and the transistor T8 side (the bottom side of paper of FIG. 3) is assumed to be the low voltage side.

Then, at time t1, because a positive voltage is caused in the first primary winding Lf1 and the excitation current (the primary side current Iin1) flows, a positive voltage is also induced in the second primary winding Lf2. However, because the battery unit BU is isolated in terms of a circuit as described earlier, an induced current does not flow in the second primary winding Lf2.

On the other hand, as time t1, a voltage is also induced in each of the secondary windings Ls1 to LsN due to the positive voltage generated in the first primary winding Lf1. Thereby, the induced current flows in each of the secondary windings (Ls1 to LsN) corresponding to a unit in the middle of consuming electric power on the secondary side.

Next, at time t2, the gate voltage controlling circuit 144 switches the gate voltages of the transistors T1 and T4 from on-level to off-level. Thereby, the voltages of the second primary winding Lf2 and each of the secondary windings Ls1 to LsN are switched to zero.

Next, at a time at which a half cycle of switching elapses from time t1, i.e. at time t3, the gate voltage controlling circuit 144 switches the gate voltages of the transistors T2 and T3 from off-level to on-level. Thereby, the primary side current Iin1 of direct-current outputted from the positive side output terminal of the rectifier 134 flows in the order of the transistor T3 first, then the first primary winding Lf1 and then the transistor T2, and returns to the negative side output terminal of the rectifier 134.

At this time, because a negative voltage is caused in the first primary winding Lf1, a negative voltage is also induced in the second primary winding Lf2. However, because the battery unit BU is separated in terms of a circuit, an induced current does not flow in the second primary winding Lf2.

On the other hand, at time t3, a voltage whose direction is opposite to the direction of the voltage during the period between time t1 and time t2 is caused in each of the secondary windings Ls1 to LsN due to the negative voltage generated in the first primary winding Lf1. Thereby, the induced current flows in each of the secondary windings (Ls1 to LsN) corresponding to a unit in the middle of consuming electric power on the secondary side.

Next, at time t4, the gate voltage controlling circuit 144 switches the gate voltages of the transistors T2 and T3 from on-level to off-level. Thereby, the voltages of the second primary winding Lf2 and each of the secondary windings Ls1 to LsN are switched to zero.

Next, at a time at which one cycle of switching elapses from time t1, i.e. at time t5, the gate voltage controlling circuit 144 switches the gate voltages of the transistors T1 and T4 from off-level to on-level again.

The above operation is repeated. As just described, an alternating voltage is generated in the first primary winding Lf1 and the alternating excitation current flows in the first primary winding Lf1 due to the periodic switching of the first switching circuit 130. Therefore, an alternating voltage is induced in each of the secondary windings Ls1 to LsN (an oppositely-oriented voltage is caused per a half cycle of switching). The alternating induced currents on the secondary side caused by this manner are rectified by the respective rectifiers 160, and the smoothed direct currents Is1, Is2, Is3, . . . Isn flow in the respective units 1 to N on the secondary side.

During the above working period of the circuit, the current detector 136 measures an electric current value of the primary side current Iin1 at constant time interval, and inputs the measured value to the power-supply controlling circuit 140. Thereby, the power-supply controlling circuit 140 calculates the amplitude of the external electric power supplied from the external power source 120. The power-supply controlling circuit 140 switches the circuit operation of the power supply system from the standby mode in FIG. 4 to the discharging mode explained with FIG. 5, when the amplitude of the supplied external electric power reaches the maximum value (the maximum value available from the external power source 120).

In addition, during the above working period of the circuit, the battery power monitoring circuit BM measures the charging voltage Vin2 of the battery unit BU at constant time interval, and inputs the measured value to the power-supply controlling circuit 140. Thereby, the power-supply controlling circuit 140 switches the circuit operation of the power supply system to the charging mode explained with FIG. 6, when the charging voltage Vin2 of the battery unit BU is lower than the voltage at completion of charging and the amplitude of the external electric power is sufficiently lower than the amplitude of the supplied external electric power.

Moreover, the feedback signals FB1 to FBN indicative of indexes of the consumed power such as the values of the electric currents supplied to the respective units 1 to N on the secondary side are inputted to the power-supply controlling circuit 140. Thereby, the power-supply controlling circuit 140 calculates and determines the duty ratio, on the basis of the feedback signals FB1 to FBN and the amplitude of the primary side current detected by the current detector 136 (the amplitude of the currently supplied external electric power).

That is, when the consumed power on the secondary side is increased, the power-supply controlling circuit 140 controls the gate voltage controlling circuit 144, in such a manner that the on-span of the transistors T1 and T4 (the period between time t1 and time t2) and the on-span of the transistors T2 and T3 (the period between time t3 and time t4) become longer. On the other hand, when the consumed power on the secondary side is decreased, the power-supply controlling circuit 140 controls the gate voltage controlling circuit 144 in such a manner that the on-span of the transistors T1, T2, T3 and T4 becomes shorter.

Note that, as an example here, it is assumed that the transistors T1 and T4 are controlled in such a manner that their on-span and off-span accord with each other as presented above. Similarly, it is assumed that the transistors T2 and T3 are controlled in such a manner that their on-span and off-span accord with each other as presented above. In addition, as an example here, it is assumed that the length of the on-span of the transistors T1 and T4 (the period between time t1 and time t2) is controlled so as to become equal to the length of the on-span of the transistors T2 and T3.

Figure 5:
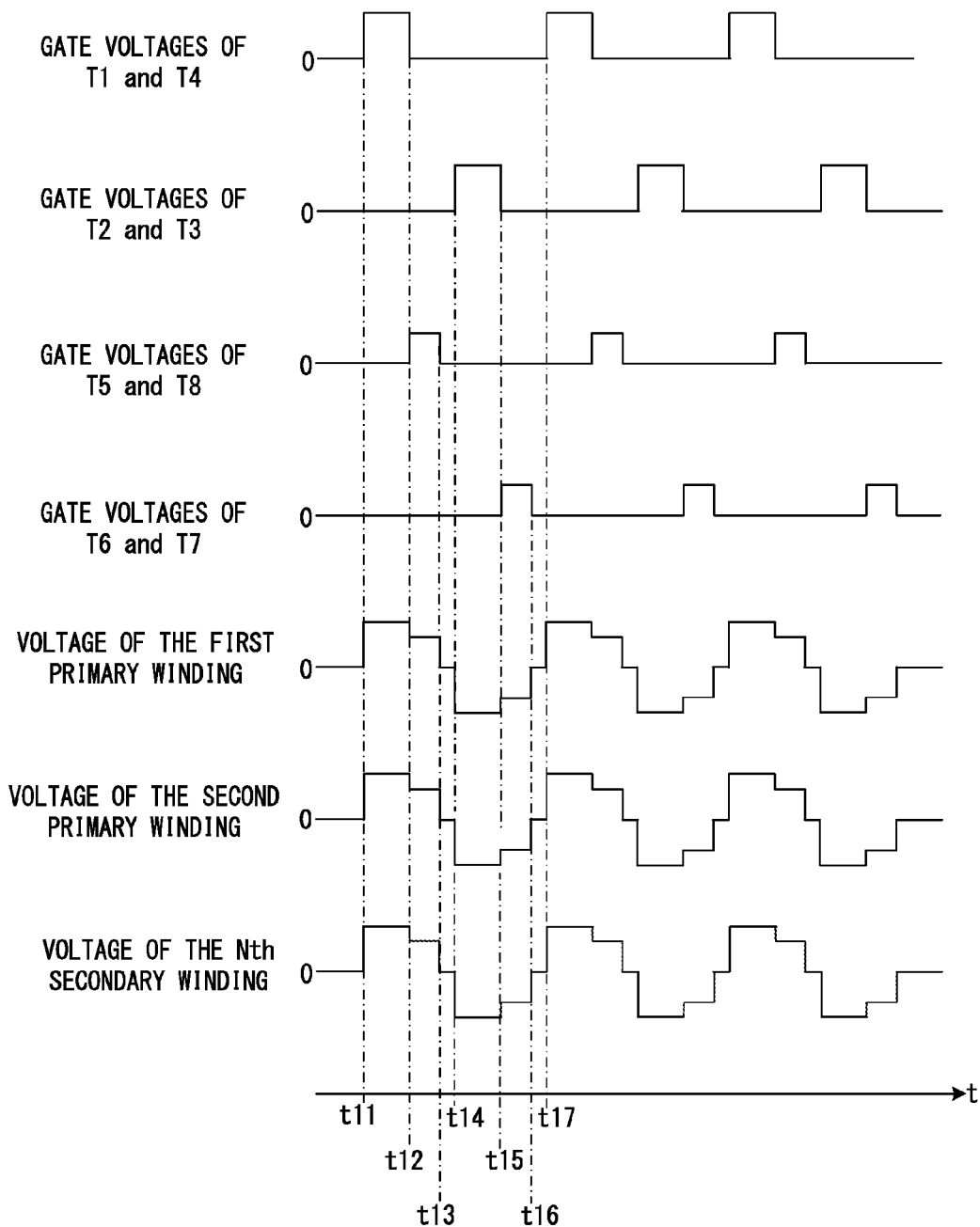
FIG. 5 is a schematic diagram showing an example of the voltage waveforms of the respective components of the electric power supply system of the MRI apparatus of the first embodiment in the way similar to FIG. 4, when the battery unit discharges.

FIG. 5 is a schematic diagram showing an example of the voltage waveforms of the respective components of the electric power supply system of the MRI apparatus 20 in the discharging mode (when the battery unit BU discharges), in the way similar to FIG. 4. In FIG. 5, each horizontal axis indicates elapsed time t.

In FIG. 5, time variations are shown for the gate voltages of the transistors T1 and T4, the gate voltages of the transistors T2 and T3, the gate voltages of the transistors T5 and T8, the gate voltages of the transistors T6 and T7, the voltage of the first primary winding Lf1, the voltage of the second primary winding Lf2, and the voltage of the N-th secondary windings Lsn, from top to bottom.

In the example of FIG. 5, the period between time t11 and time t17 is one cycle of switching, the period between time t11 and time t14 is a half cycle of switching, and the period between time t14 and time t17 is a half cycle of switching.

In addition, the period between time t13 and time t14 and the period between time t16 and time t17 are dead times during which all the transistors T1 to T8 are turned off.

Note that, the dead time during which all the transistors T1 to T8 are turned off is inserted (set) in a half cycle of switching regardless of execution of discharge or charge.

As described earlier, in the discharging mode, the on-spans of the transistors T1 to T4 in one cycle are fixed to the upper limit Onmax, and apart of the consumed power on the secondary side (shortfall beyond the external electric power) is covered with the discharging current from the battery unit BU.

Thus, in the discharging mode, the current controller 152 keeps the switch SW1 at the conductive state, and electrically blocks out the route between the diode D9 and the positive terminal side of the battery unit BU. Thereby, though outputting of the discharging current from the battery unit BU is enabled via the diode D10, the discharging current never flows into the positive terminal side of the battery unit BU via the diode D9.

In the following, the circuit operation of the discharging mode (the case where the battery unit BU discharges) will be explained by reference to time t11 to time t17 shown in FIG. 5.

Firstly, at time t11, the gate voltage controlling circuit 144 switches the gate voltages of the transistors T1 and T4 from off-level to on-level, in the aforementioned manner. Thereby, the primary side current Iin1 outputted from the rectifier 13 flows in the first primary winding Lf1 as the excitation current in the aforementioned manner.

At this time, because a positive voltage is caused in the first primary winding Lf1, voltages are induced in the second primary winding Lf2 and each of the secondary windings Ls1 to LsN. However, out of the transistors T1 to T8, the transistors excluding the transistors T1 and T4 are turned off during the period between time t11 and time t12, and thus an induced current does not flow in the second primary winding Lf2.

On the other hand, at time t11, because a voltage is generated in each of the secondary windings Ls1 to LsN in the aforementioned manner, the induced current flows in each of the secondary windings (Ls1 to LsN) corresponding to units in the middle of consuming electric power on the secondary side.

Next, at time t12, the gate voltage controlling circuit 144 switches the gate voltages of the transistors T1 and T4 from on-level to off-level. In synchronization with the timing immediately after the gate voltages of the transistors T1 and T4 become off-level, the gate voltage controlling circuit 156 switches the gate voltages of the transistors T5 and T8 from off-level to on-level.

Thereby, a discharging current is outputted from the positive terminal side of the battery unit BU. This discharging current flows as the excitation current in the order of the switch SW1 first, then the diode D10, then the transistor T5, then the second primary winding Lf2, and then the transistor T8, and returns to the negative terminal side of the battery unit BU.

Therefore, a positive voltage is generated in the second primary winding Lf2. The voltage of the second primary winding Lf2 during the period between this time t12 and time t13 corresponds to the charging voltage Vin2 of the battery unit BU, and thus it is lower than the voltage for the sake of charging the battery unit BU (the voltage of the second primary winding Lf2 during the period between time t11 and time t12). This is because the winding numbers of the first primary winding Lf1 and the second primary winding Lf2 satisfy the aforementioned electrifiable condition.

In the period between time t12 and time t13 during which a positive voltage is generated in the second primary winding Lf2 due to the discharging current, a positive voltage is also induced in the first primary winding Lf1, and a voltage is induced in each of the secondary windings Ls1 to LsN. However, because the transistors T1 to T4 are turned off during the period between time t12 and time t13, an induced current does not flow in the first primary winding Lf1. On the other hand, the induced current flows in each of the secondary windings (Ls1 to LsN) corresponding to units in the middle of consuming electric power on the secondary side.

Next, at time t13, the gate voltage controlling circuit 156 switches the gate voltages of the transistors T5 and T8 from on-level to off-level. After this, the dead time continues until time t14.

Next, at time t14 at which a half cycle of switching elapses from time t11, the gate voltage controlling circuit 144 switches the gate voltages of the transistors T2 and T3 from off-level to on-level in the aforementioned manner. Therefore, the primary side current Iin1 flows as the excitation current in the first primary winding Lf1 in the aforementioned manner, and a negative voltage is generated in the first primary winding Lf1. Thereby, a negative voltage is induced in the second primary winding Lf2, and in each of the secondary windings Ls1 to LsN, a voltage whose polarity is opposite to the voltage during the period between time t11 and time t12 is induced.

Thus, at time t14, the induced current whose direction is opposite to that during the period between time t11 and time t12 flows in each of the secondary windings (Ls1 to LsN) corresponding to units in the middle of consuming electric power on the secondary side. Note that, an induced current does not flow in the second primary winding Lf2 during the period between time t14 and time t15, for the same reason as the period between time t11 and time t12.

Next, at time t15, the gate voltage controlling circuit 144 switches the gate voltages of the transistors T2 and T3 from on-level to off-level. In synchronization with the timing immediately after the gate voltages of the transistors T2 and T3 become off-level, the gate voltage controlling circuit 156 switches the gate voltages of the transistors T6 and T7 from off-level to on-level.

Thereby, a discharging current is outputted from the positive terminal side of the battery unit BU. This discharging current flows as the excitation current in the order of the diode D10 first, then the transistor T7, then the second primary winding Lf2, then the transistor T6, and returns to the negative terminal side of the battery unit BU. Therefore, a negative voltage is generated in the second primary winding Lf2 during the period between time t15 and time t16. Thereby, a negative voltage is induced in the first primary winding Lf1, and in each of the secondary windings Ls1 to LsN, a voltage whose polarity is opposite to the voltage during the period between time t12 and time t13 is induced.

However, because the transistors T1 to T4 are turned off during the period between time t15 and time t16, an induced current does not flow in the first primary winding Lf1. On the other hand, the induced current whose direction is opposite to that during the period between time t12 and time t13 flows in each of the secondary windings (Ls1 to LsN) corresponding to units in the middle of consuming electric power on the secondary side.

Next, at time t16, the gate voltage controlling circuit 156 switches the gate voltages of the transistors T6 and T7 from on-level to off-level. After this, the dead time continues unit time t17.

Next, at time t17 at which one cycle of switching elapses from time t11, the gate voltage controlling circuit 144 switches the gate voltages of the transistors T1 and T4 from off-level to on-level in the aforementioned manner. The above operation is repeated.

As just described, the external electric power flows the first primary winding Lf1 as the alternating excitation current due to the periodic switching of the first switching circuit 130, and the accumulated power of the battery unit BU flows the second primary winding Lf2 as the alternating excitation current due to the periodic switching of the second switching circuit 148. Thereby, the alternating induced current is generated in each of the secondary windings Ls1 to Lsn.

Here, the electric currents Is1 to IsN supplied to the respective units 1 to N on the secondary side are smoothed through one cycle of switching between time t11 and time t17. Therefore, the electric current amount on the secondary side in the discharging mode is larger than that in the standby mode, by the amount of the induced currents flowing the secondary side during the period between time t12 and time 13 and the period between time t15 and time t16.

In other words, the electric current on the secondary side in the discharging mode is larger than the external electric power transmitted via the first primary winding Lf1, by the amount of the induced current flowing during the period between time t12 and time 13 and the period between time t15 and time t16 due to the discharging current from the battery unit BU as the excitation current. Thus, the shortfall of the consumed power on the secondary side beyond the external electric power is covered with discharge of the accumulated power of the battery unit BU in the discharging mode.

Figure 6:
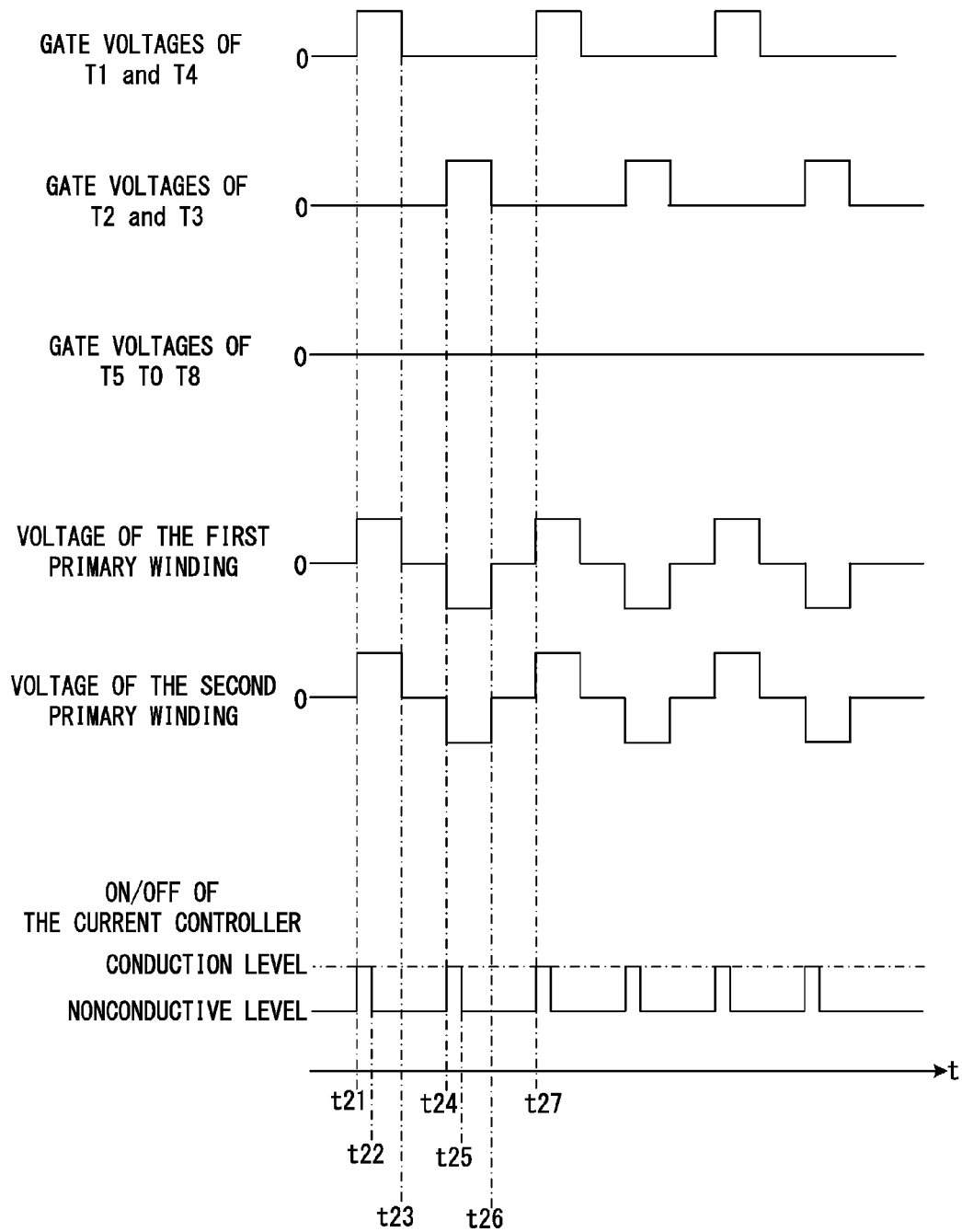
FIG. 6 is a schematic diagram showing an example of the voltage waveforms of the respective components of the electric power supply system of the MRI apparatus of the first embodiment in the way similar to FIG. 4, when the battery unit is charged.

FIG. 6 is a schematic diagram showing an example of the voltage waveforms of the respective components of the electric power supply system of the MRI apparatus 20 in the charging mode (when the battery unit BU is charged), in the way similar to FIG. 4. In FIG. 6, each horizontal axis indicates elapsed time t.

In FIG. 6, time variations are shown for the gate voltages of the transistors T1 and T4, the gate voltages of the transistors T2 and T3, the gate voltages of the transistors T5 to T8, the voltage of the first primary winding Lf1, the voltage of the second primary winding Lf2, and the on/off state the current controller 152, from top to bottom.

In the charging mode, the gate voltage controlling circuit 156 keeps the transistors T5 to T8 at off-state on a steady basis. In addition, in the charging mode, the current controller 152 prevents the discharging current from flowing from the positive terminal side of the battery unit BU via the diode D10, by constantly keeping the switch SW1 at nonconductive state.

In the example of FIG. 6, the current controller 152 restricts inflow amount of the charging current to the battery unit BU, by turning on not "in the entire period during which a voltage is induced in the second primary winding Lf2" but in a part of this period. This is because the impedance of the battery unit BU in time of charging is very low and it is preferable to protect the battery unit BU by restricting electric current.

In addition, in the example of FIG. 6, the period between time t21 and time t27 is one cycle of switching, the period between time t21 and time t24 is a half cycle of switching, and the period between time t24 and time t27 is a half cycle of switching.

In the charging mode, the alternating excitation current flows the first primary winding Lf1 due to the periodic switching of the first switching circuit 130. The alternating induced current generated in the second primary winding Lf2 by this manner go through either the regeneration diodes D5 and D8 or the regeneration diodes D6 and D7, and flows into the battery unit BU in the same direction.

In the following, the circuit operation of the charging mode (the case where the battery unit BU is charged) will be explained by reference to time t21 to time t27 shown in FIG. 6.

Firstly, at time t21, the gate voltage controlling circuit 144 switches the gate voltages of the transistors T1 and T4 from off-level to on-level in the aforementioned manner. Thereby, because a positive voltage is caused in the first primary winding Lf1 in the aforementioned manner, a positive voltage is induced in the second primary winding Lf2 and a voltage is induced in each of the secondary windings Ls1 to LsN. Thus, in the secondary side, the induced currents flows in the same manner as the standby mode.

Here, at time t21, in synchronization with the timing at which the gate voltages of the transistors T1 and T4 switch to on-level, the current controller 152 switches from the nonconductive state to the conductive state (turns on). Therefore, an induced current (a charging current) flows in the order of the negative terminal side of the battery unit BU first, then the regeneration diode D6, then the second primary winding Lf2, then the regeneration diode D7, then the diode D9, then the current controller 152, and then the positive terminal side of the battery unit BU, due to the positive voltage induced in the second primary winding Lf2. Thereby, the battery unit BU is charged.

Next, at time t22 in the on-span of the transistors T1 and T4, the current controller 152 switches from the conductive state to the nonconductive state (turns off). Thereby, inflow of the charging current into the battery unit BU is blocked out, and an electric current does not flow in the second primary winding Lf2.

Next, at time t23, the gate voltage controlling circuit 144 switches the gate voltages of the transistors T1 and T4 from on-level to off-level. Thereby, the voltage having been induced in each of the secondary windings Ls1 to LsN becomes zero level.

Next, at time t24 at which a half cycle of switching elapses from time t21, the gate voltage controlling circuit 144 switches the gate voltages of the transistors T2 and T3 from off-level to on-level in the aforementioned manner. Thereby, because a negative voltage is induced in the first primary winding Lf1, a negative voltage is induced in the second primary winding Lf2 and a voltage is induced in each of the secondary windings Ls1 to LsN. Thus, induced currents flow in the secondary side in the way similar to the standby mode.

In addition, at time t24, in synchronization with the timing at which the gate voltages of the transistors T2 and T3 switch to on-level, the current controller 152 turns on. Therefore, an induced current (a charging current) flows in the order of the negative terminal side of the battery unit BU first, then the regeneration diode D8, then the second primary winding Lf2, then the regeneration diode D5, then the diode D9, then the current controller 152, and then the positive terminal side of the battery unit BU, due to the negative voltage induced in the second primary winding Lf2. Thereby, the battery unit BU is charged.

Next, at time t25 in the on-span of the transistors T2 and T3, the current controller 152 turns off, the charging current is blocked out, and an electric current does not flow in the second primary winding Lf2.

Next, at time t26, the gate voltage controlling circuit 144 switches the gate voltages of the transistors T2 and T3 to off-level. Thereby, the voltage having been induced in each of the secondary windings Ls1 to LsN becomes zero level.

Next, at time t27 at which one cycle of switching elapses from time t21, each component operates in the way similar to time t21. The battery unit BU is charged during on-span of the current controller 152 by repeating the above operation.

During the above switching operation, the power-supply controlling circuit 140 controls the length of the on-span of the current controller 152, in accordance with the duty ratio of the transistors T1 to T4, the impedance of the battery unit BU at charging and the like.

That is, the power-supply controlling circuit 140 sets the length of the on-span of the current controller 152 so as not to exceed the length of the on-span of the transistors T1 to T4, and stops charging in accordance with the charging voltage of the battery unit BU inputted from the battery power monitoring circuit BM and so on. For example, at the timing when the charging voltage of the battery unit BU reaches the voltage Vin2$m$ at completion of charging, the power-supply controlling circuit 140 switches the power supply system of the MRI apparatus 20 from the charging mode to the standby mode.

Next, the circuit size of the first primary winding Lf1 side such as the rectifier 134, the capacitor C1, the first switching circuit 130 and the like (the part of transmitting the external electric power from the external power source 120 to the secondary side) will be explained.

The amount of the consumed power during implementation term of an imaging sequence differs by type of sequence. As examples of the imaging sequences which require especially large electric power, EPI (Echo Planar Imaging), three-dimensional FFE (fast field echo), and SSFP (steady-state free precession) targeting a cardinal region as an imaging part are included.

Thus, it is preferable to cover the consumed power with the accumulated electric power of the battery unit BU and the external electric power during implementation term of an imaging sequence which requires a large amount of the consumed power as just described, and it is preferable to make an imaging sequence practicable by using only the external electric power in the case of an imaging sequence which requires a standard amount of the consumed power.

This is because the circuit size of the first primary winding Lf1 side can be downsized to a just enough size to output the consumed power of the threshold TH on a steady basis if a standard amount of the consumed power is approximately equal to the threshold TH in FIG. 1. In this case, the power supply system of the MRI apparatus 20 operates in the standby mode or the charging mode during an imaging sequence whose consumed power is around a standard amount.

In addition, it is preferable to measure the charging voltage of the battery unit BU Vin2 at constant time interval and charge the battery unit BU by switching the power supply system to the charging mode in, for example, the following period if the measured voltage does not reach the voltage at completion of charging. More specifically, it is desired that the power-supply controlling circuit 140 automatically switch the power supply system to the charging mode so as to charge the battery unit BU until completion of charging while the MRI apparatus 20 is unoccupied such as night time, or while an imaging sequence is not performed such as a period of replacing an object.

Next, the method of judging whether an imaging sequence is practicable or not by the system control unit 52 will be explained. Before performing this judgment, the system control unit 52 calculates the estimated time variation of the consumed power in the case of performing the imaging sequence of the main scan in accordance with the set conditions.

The system control unit 52 preliminarily stores, for example, various patterns of conditions of an imaging sequence per type of pulse sequences such as EPI and the estimated time variation of the consumed power in each pattern. The estimated time variation of the consumed power in each pattern can be obtained by preliminarily calculating or measuring under simulation.

The above each pattern is an estimated time variation of the consumed power for representative values (representative conditions) of the respective parameters of conditions of the imaging sequence. The system control unit 52 preliminarily stores the respective estimated time variations for various representative values, and selects one whose conditions are the closest to the imaging sequence set in Step S1, out of these estimated time variations.

The system control unit 52 modifies the estimated time variation of the consumed power of the selected pattern, on the basis of the difference in conditions between the imaging sequence of the selected pattern and the set imaging sequence. By this modification, the system control unit 52 calculates the estimated time variation of the consumed power in the case of performing the imaging sequence of the main scan in accordance with the set conditions.

Note that, the above calculation method is only an example and other methods may be alternatively used. For example, an estimated time variation of consumed power may be calculated by using an equivalent circuit model of the gradient magnetic field power supply 44 and the gradient magnetic field coil 26 and substituting the conditions of the imaging sequence into the equivalent circuit model. This is because the gradient magnetic field power supply 44 and the gradient magnetic field coil 26 have the maximum consumed power and the maximum variation of the consumed power in the MRI apparatus 20 in time of acquiring the MR signals such as a main scan, in general.

As an example here, practicability of an imaging sequence is judged by determining whether the following two conditions are satisfied or not, on the basis of the remaining battery level of the battery unit BU and the time variation of the estimated consumed power.

The first condition is that there is not any timing at which the (momentary) maximum value in the estimated time variation of the consumed power exceeds the maximum value of available output power. The available output power means the sum of the maximum value of the external electric power supplied from the external power source 120 in FIG. 3 and electric power of the discharging current from the battery unit BU. For example, it is judged whether the sum of the maximum value of the external electric power and the maximum value of the discharging current available from the battery unit BU falls below the maximum value PK of the estimated consumed power in FIG. 1 or not.

The second condition is that the total consumed power through implementation term of an imaging sequence does not exceeds the sum of the external electric power amount supplied through the implementation term and the accumulated electric power (remaining battery level) of the battery unit BU. As an example, consider a case where the period between time ta and time tb in FIG. 1 is an implementation term of an imaging sequence. In this case, conceptually, it is judged whether or not a time integral value of consumed power between time ta and time tb exceeds the sum of the external electric power amount supplied during the period between time ta and time tb and the accumulated electric power of the battery unit BU.

If the above two conditions are satisfied, the system control unit 52 judges the imaging sequence to be practicable. If this is not the case, the system control unit 52 judges the imaging sequence to be impracticable. When the system control unit 52 judges the imaging sequence to be impracticable, the system control unit 52 calculates correction options of conditions of the imaging sequence or restricts conditions of the imaging sequence. After this, the system control unit 52 makes the display device 64 display a screen for setting conditions of the imaging sequence again with a warning.

Note that, though even the above flow is sufficient, as an example in the flow of the later-described FIG. 8, it is controlled in the following manner if the imaging sequence is judged to be impracticable. That is, the system control unit 52 judges whether or not there is an imaging sequence next to the imaging sequence judged to be impracticable. Then, the system control unit 52 judges whether or not the next imaging sequence is practicable satisfying the above first condition and the second condition and has a margin of electric power enough for switching to the charging mode during its implementation term.

If the judging result is affirmative, the system control unit 52 makes the display device 64 display a message requiring an order change of the imaging sequences. After this, if an input of permitting the order change is inputted, the system control unit 52 changes the order in such a manner that the imaging sequence next to the imaging sequence judged to be impracticable is performed in front. Thereby, the charging period can be longer even if only slightly.

As to the calculation of the correction options of conditions of the imaging sequence, the system control unit 52 calculates the correction options so as to reduce consumed power to a degree of satisfying the above two conditions, for example. In order to reduce consumed power amount, i.e. reduce electric load, for example, decreasing a slice number, expanding field of view, lowering resolution by decreasing step numbers of the phase encode direction and the frequency encode direction and so on are included.

Thereby, for example, a slice number which is set fewer than the current setting value so as to satisfy the above two conditions, step numbers of the phase encode direction and the frequency encode direction decreased to a degree of satisfying the above two conditions or the like are calculated as the correction options of conditions.

Figure 7:
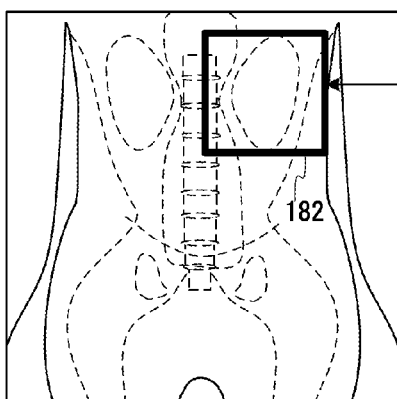
FIG. 7 is a schematic diagram showing an example of an input screen for setting conditions of an imaging sequence again, when an imaging sequence is judged to be impracticable.

FIG. 7 is a schematic diagram showing an example of an input screen for setting conditions of an imaging sequence again, when an imaging sequence is judged to be impracticable. As shown in FIG. 7, as an example here, a warning display indicating that the imaging sequence is impracticable is textually added on the top of the screen.

In addition, a frame 182 of FOV (Field Of View) is displayed inside a scout image 180, and boxes 184, 190, 194 and 196 for setting imaging conditions are displayed on the right side of the scout image 180.

In the example of FIG. 7, it is displayed in the box 184 as one correction option of the conditions of the imaging sequence to expand FOV from 125 mm×125 mm to 150 mm×150 mm. In addition, it is displayed in the box 190 as one correction option of the conditions of the imaging sequence to decrease the slice number from 100 to 50.

In addition, it is displayed in the box 194 and 196 as one correction option of the conditions of the imaging sequence to decrease the phase encode step number and the frequency encode step number from 256 to 128 respectively.

A user can reconfigure the conditions of the imaging sequence by selecting one or a plurality of the correction options of the conditions of the imaging sequence displayed on the display device 64 via the input device 62 so as to make the imaging sequence practicable.

As an example here, when the system control unit 52 judges the imaging sequence to be impracticable, the system control unit 52 restricts the settable range of the conditions of the imaging sequence so as not to increase the consumed power. Concretely speaking, for example, the system control unit 52 restricts each condition (parameter) of the imaging sequence in such a manner that a value or the like giving a larger consumed power than that given by the currently set value or the like cannot be inputted.

For example, if an operator inputs a value larger than the currently set 100 as to the slice number, the system control unit 52 may make the display device 64 perform an error display. As just described, the display device 64 displays an input screen whose settable range is restricted by the system control unit 52 in the above manner, as an input screen for setting the conditions of the imaging sequence again.

Figure 8:
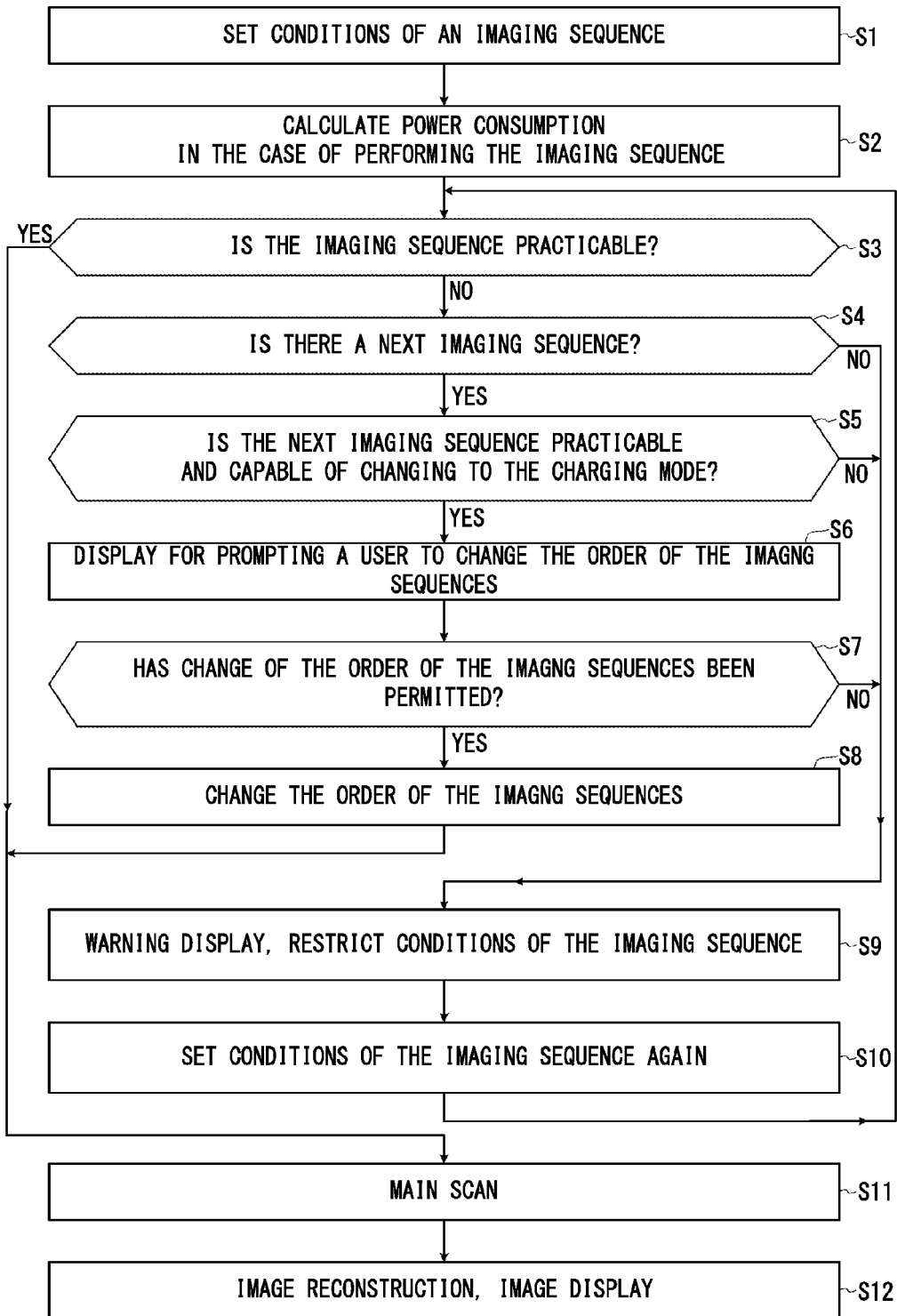
FIG. 8 is a flowchart illustrating an example of a flow of a process performed by the MRI apparatus of the first embodiment.

FIG. 8 is a flowchart illustrating an example of a flow of an imaging operation performed by the MRI apparatus 20 of the first embodiment. As an example here, it is assumed that the power-supply controlling circuit 140 in FIG. 3 is a part of the system control unit 52 in FIG. 2.

That is, the charging voltage Vin2 of the battery unit BU is inputted from the battery power monitoring circuit BM to the system control unit 52 on a steady basis, the feedback signals FB1 to FBN are inputted from the respective units 1 to N to the system control unit 52 on a steady basis, and the value of the primary side current Iin1 is inputted from the current detector 136 to the system control unit 52 on a steady basis. The above "on a steady basis" means, for example, a predetermined time interval which is short enough to judge the variation of increase or decrease of the electric currents in the respective components in terms of the circuit operation.

Thus, during implementation term of the processing of Step S1 to Step S12 in FIG. 8, the power-supply controlling circuit 140 of the system control unit 52 switches the operation of the power supply system from one of the charging mode, the discharging mode and the standby mode to another of them.

That is, even in the middle of performing the imaging sequence, the power-supply controlling circuit 140 of the system control unit 52 charges the battery unit BU with the external electric power by switching to the charging mode, if the consumed power on the secondary side is smaller than the maximum value of the external electric power and the charging voltage Vin2 of the battery unit BU has not reached the voltage at completion of charging.

Possible cases of switching to the discharging mode are, for example, the implementation term of the main scan in Step 11 in FIG. 8 and a case of performing a prescan under a method involving a large consumed power. As an example of a prescan whose consumed power is large, a template shot for obtaining phase correction data in EPI (see Japanese Patent Application Laid-open (KOKAI) Publication No. 9-2762439) is included.

In the following, according to the step numbers in the flowchart shown in FIG. 8, an imaging operation of the MRI apparatus 20 will be described by referring to each of the aforementioned drawings as required.

[Step S1] The system control unit 52 (see FIG. 2) sets some of conditions of the imaging sequence of the main scan on the basis of conditions of the imaging sequence inputted to the MRI apparatus 20 via the input device 62. In addition, other conditions of the imaging sequence such as a center frequency of RF pulses are set by performing heretofore known prescans. By this manner, the system control unit 52 provisionally sets all the conditions of the imaging sequence of the main scan. After this, the process proceeds to Step S2.

[Step S2] The system control unit 52 calculates an estimated time variation of the consumed power in the case of performing the imaging sequence of the main scan under the conditions set in Step S1, in the aforementioned manner. After this, the process proceeds to Step S3.

[Step S3] The system control unit 52 calculates the accumulated electric power (remaining battery level) of the battery unit BU, on the basis of the updated charging voltage Vin2 inputted from the battery power monitoring circuit BM. The system control unit 52 judges whether the aforementioned two conditions are satisfied or not, on the basis of the accumulated electric power of the battery unit BU and the estimated time variation of the consumed power calculated in Step S2.

The first condition is that there is not any timing at which the (momentary) maximum value in the estimated time variation of the consumed power exceeds the maximum value of the available output power.

The second condition is that the total consumed power through implementation term of the imaging sequence does not exceed the sum of the external electric power amount supplied through the implementation term and the accumulated electric power of the battery unit BU.

If the above two conditions are satisfied, the system control unit 52 decides on using all the provisionally set conditions of the imaging sequence as determined conditions, and then proceeds to Step S11.

If at least one of the above two conditions are not satisfied, the system control unit 52 proceeds to Step 4. However, if the above judgment has been performed on the basis of a voltage lower than the voltage of the battery unit BU at completion of charging, the system control unit 52 may perform rejudgement in the following manner.

That is, the system control unit 52 assumes that the charging voltage Vin2 of the battery unit BU is the voltage at completion of charging, and rejudge whether the above two conditions are satisfied or not. If the above two conditions are satisfied in the rejudgement, the system control unit 52 completes charging of the battery unit BU by switching the power supply system to the charging mode and then proceeds to Step S6. If at least one of the above two conditions are not satisfied in the rejudgement, the system control unit 52 proceeds to Step S4.

[Step S4] The system control unit 52 judges whether an imaging sequence next to the imaging sequence judged to be impracticable in Step S3 exists or not. As an example here, it is assumed that the imaging sequence judged to be impracticable in Step S3 and the imaging sequence next to that are imaging sequences for the same object.

If the next imaging sequence exists, the system control unit 52 proceeds to Step S5. If this is not the case, the system control unit 52 proceeds to Step S9.

[Step S5] The system control unit 52 judges whether or not the imaging sequence next to the imaging sequence judged to be impracticable in Step S3 satisfies both of the condition A and the condition B as follows.

The condition A is that the next imaging sequence is practicable by satisfying the first condition and the second condition explained in Step S3. The condition B is that there is a margin of electric power to switch to the charging mode during its implementation term if the next imaging sequence is performed in first.

If both of the condition A and the condition B are satisfied, the system control unit 52 proceeds to Step S6. If this is not the case, the system control unit 52 proceeds to Step S9.

[Step S6] The system control unit 52 makes the display device 64 display a message requiring an order change of the imaging sequences. More specifically, it is a display of requiring permission for performing the imaging sequence next to the imaging sequence judged to be impracticable in Step S3 in first and then performing the imaging sequence judged to be impracticable in Step S3.

After this, the process proceeds to Step S7.

[Step S7] If an operator enters an input of permitting the order change of the imaging sequence to the input device 62 in Step S6, the system control unit 52 proceeds to Step S8. If this is not the case, the system control unit 52 proceeds to Step S9.

[Step S8] The system control unit 52 changes the order of the imaging sequences. That is, the imaging sequence judged to satisfy both of the condition A and the condition B in Step S5 is performed in first, and subsequently, the imaging sequence judged to be impracticable in Step S3 is performed. After this, the process proceeds to Step S11.

[Step S9] The system control unit 52 calculates correction options of the conditions of the imaging sequence so as to satisfy the above two conditions explained in Step S3, for example. In addition, the system control unit 52 makes the display device 64 display a screen for setting the respective conditions of the imaging sequence again with the aforementioned warning (see FIG. 7).

Note that, the conditions of the imaging sequence may be restricted by other methods, instead of displaying the correction options of the conditions of the imaging sequence. For example, input for the respective conditions of the imaging sequence may be restricted so as not to increase the consumed power more than the current setting values. For example, in the case of a slice number, input is restricted in such a manner that a value larger than the current setting value cannot be inputted. For example, in the case of FOV, input is restricted in such a manner that a range narrower than the current range cannot be set. After this, the process proceeds to Step S10.

[Step S10] At least one or some of the conditions of the imaging sequence is (are) set again by an operator. The system control unit 52 provisionally sets all the conditions of the imaging sequence again, on the basis of the reconfigured condition and an execution result of a prescan or the like. After this, the process returns to Step S2, and an estimated time variation of the consumed power in the case of performing the imaging sequence whose conditions are set again is calculated.

That is, (1) provisional setting of conditions of the imaging sequence, (2) calculation of an estimated time variation of the consumed power in the case of performing the provisionally set imaging sequence and (3) the judgment processing as to whether the above two conditions are satisfied or not, are repeated in order, until the above two conditions explained in Step S3 are satisfied.

[Step S11] The main scan is performed, according to the conditions of the imaging sequence judged to satisfy the above two conditions explained in Step S3. Note that, if the order of imaging sequences are changed in Step S8, the main scan here means the imaging sequence to be performed foremost due to the order change.

More specifically, the object P is loaded on the table 32*a*, and a static magnetic field is formed in the imaging space by the static magnetic field magnet 22 in the main scan. In addition, electric currents are supplied from the shim coil power supply 42 to the shim coil 24, thereby the static magnetic field formed in the imaging space is uniformed. Then, when the system control unit 52 receives a command of start of imaging from the input device 62, the system control unit 52 drives the gradient magnetic field power supply 44, the RF transmitter 46 and the RF receiver 48 in accordance with the determinate conditions of the imaging sequence, thereby a gradient magnetic field is formed in the imaging region, which includes the imaging part of the object P, and RF pulses are generated from the transmission RF coil 28.

Thus, MR signals generated by nuclear magnetic resonance inside the object P are detected by the reception RF coil 29 and the RF coil device 100, and received by the RF receiver 48. The RF receiver 48 performs predetermined signal processing on the detected MR signals and then performs A/D conversion on the MR signals so as to generate raw data which are digitized MR signals. The RF receiver 48 inputs the generated raw data of the MR signals to the image reconstruction unit 56. The image reconstruction unit 56 stores the raw data, as the k-space data. After this, the process proceeds to Step S12.

[Step S12] The image reconstruction unit 56 reconstructs image data by performing image reconstruction processing including Fourier transformation on the k-space data, and stores the reconstructed image data in the image database 58. The image processing unit 60 obtains the image data from the image database 58, generates display image data for two-dimensional display by performing predetermined image processing on the obtained image data, and stores these display image data in the storage device 66.

The system control unit 52 inputs the display image data from the storage device 66 to the display device 64, and makes the display device 64 display images indicated by the display image data.

The foregoing is a description of an operation of the MRI apparatus 20 according to the first embodiment.

As just described, the MRI apparatus 20 of the first embodiment is a hybrid-type which operates on the basis of the external electric power supplied from the external power source and the accumulated electric power of the battery unit BU charged by the external electric power. Thus, it can operate by using the accumulated electric power of the battery unit BU and the external electric power in the case of performing an imaging sequence whose consumed power is large, and it can operate by using only the external electric power in other cases.

In the above configuration, the maximum value of the external electric power supplied from the external power source 120 can be decreased by the amount of the accumulated electric power of the battery unit BU, without reducing the maximum consumed power. Thus, as described earlier with FIG. 1, a power-supply facility can be downsized without restricting conditions of an imaging sequence further than conventional technology (without reducing the maximum consumed power).

In addition, the MRI apparatus 20 of the first embodiment judges practicability of an imaging sequence before its performance, and sets the conditions the imaging sequence again with a warning display in the case of judging it impracticable. Thus, a situation in which an imaging sequence is discontinued in the middle of its performance because of shortage of the remaining battery level never happens.

Moreover, the MRI apparatus 20 of the first embodiment calculates and displays the correction options of the conditions of the imaging sequence, in the case of judging the imaging sequence to be impracticable. Thus, an operator can easily set conditions of an unfailingly practicable imaging sequence.

As an example in the present embodiment, the charging period is preserved before the imaging sequence judged to be impracticable, by inserting the processing of Step S4 to Step S8 and replacing the order of it with the order of the next imaging sequence on the premise of the permission from an operator. Thus, there is a merit of eliminating the need for correction of the conditions of the imaging sequence by changing the order of the imaging sequences.

According to the aforementioned embodiment, a power-supply facility can be downsized without reducing the maximum consumed power in an image diagnosis apparatus such as an MRI apparatus. Note that, the technological thought of the first embodiment in which the image diagnosis apparatus is configured as a hybrid-type and the charge/discharge element for power supply is charged during imaging if possible never exists in conventional technology.

<Supplementary Notes on the First Embodiment>

[1] The above processing of Step S4 to Step S8 is not essential and may be omitted. That is, if the imaging sequence is judged to be impracticable in Step S3, the process may directly proceed to Step S9.

[2] In the first embodiment, an example in which switching of the charging mode, the discharging mode and the standby mode is performed in accordance with the feedback signals FB1 to FBN from each of the units 1 to N has been explained. However, embodiments of the present invention are not limited to such an aspect.

As an example, switching of the charging mode, the discharging mode and the standby mode may be performed in accordance with the conditions of the imaging sequence and the feedback signals FB1 to FBN. In the following, control of this case will be explained.

The estimated time variation of the consumed power during implementation term of the imaging sequence is calculated in the aforementioned manner in accordance with the conditions of the imaging sequence. Thus, during implementation term of the main scan in Step S11, the power-supply controlling circuit 140 can perform switching between the charging mode, the discharging mode and the standby mode on the basis of the estimated time variation of the consumed power calculated in Step S2.

For example, the power-supply controlling circuit 140 separates the entire period into a period during which the consumed power of the MRI apparatus 20 is insufficient beyond the maximum value of the external electric power available from the external power source 120 and the other periods, on the basis of the estimated time variation of the consumed power. In this case, the power-supply controlling circuit 140 switches to the discharging mode in the period of running short of the consumed power beyond the external electric power, and switches to either the standby mode or the charging mode in the other periods in accordance with the charging voltage Vin2 of the battery unit BU.

That is, as to the periods during which the consumed power is sufficiently covered with the external electric power, the power-supply controlling circuit 140 switches to the standby mode in the case where the charging voltage Vin2 of the battery unit BU is the voltage Vin2$m$ at completion of charging, and switches to the charging mode in other cases.

As just described, when switching between the above three modes is performed on the basis of (the estimated time variation of the consumed power calculated from) the conditions of the imaging sequence, it is preferable to control, for example, in the following manner considering the deviation between the estimated time variation of the consumed power as calculation values and the actual consumed power.

That is, the power-supply controlling circuit 140 preliminarily determines the timing of switching to the discharging mode specified with a predetermined time width on the basis of the estimated time variation of the consumed power, before performance of the imaging sequence. After start of performance of the imaging sequence, the power-supply controlling circuit 140 accurately calculates and determines Hat which timing in the above predetermined time width 'switching to the discharging mode should be performed' on a real-time basis, on the basis of the actual consumed power of the MRI apparatus 20 calculated from the feedback signals FB1 to FBN. The same applies to the timing of switching to the charging mode and the timing of switching to the standby mode.

As another example, the power-supply controlling circuit 140 may control a case of switching to the charging mode in at least a part of the implementation term of an imaging sequence and a case where switching to the charging mode is not performed in the implementation term of an imaging sequence, on the basis of the type of the imaging sequence.

In this case, the power-supply controlling circuit 140 controls in such a manner that switching to the charging mode is not performed in the implementation term of the imaging sequence whose consumed power amount is calculated to be exceeding a predetermined amount, for example, EPI. On the other hand, the power-supply controlling circuit 140 controls in such a manner that switching to the charging mode is performed in at least apart of the implementation term of the imaging sequence whose consumed power amount is calculated to be below the predetermined amount (in this case, the conditions for switching to the charging mode are the same as before).

As just described, if it can be separated into a case of charging and a case where charging is not performed on the basis of the type of an imaging sequence, the power-supply controlling circuit 140 can reduce the calculation load of control of switching between the charging mode, the discharging mode and the standby mode.

Figure 9:
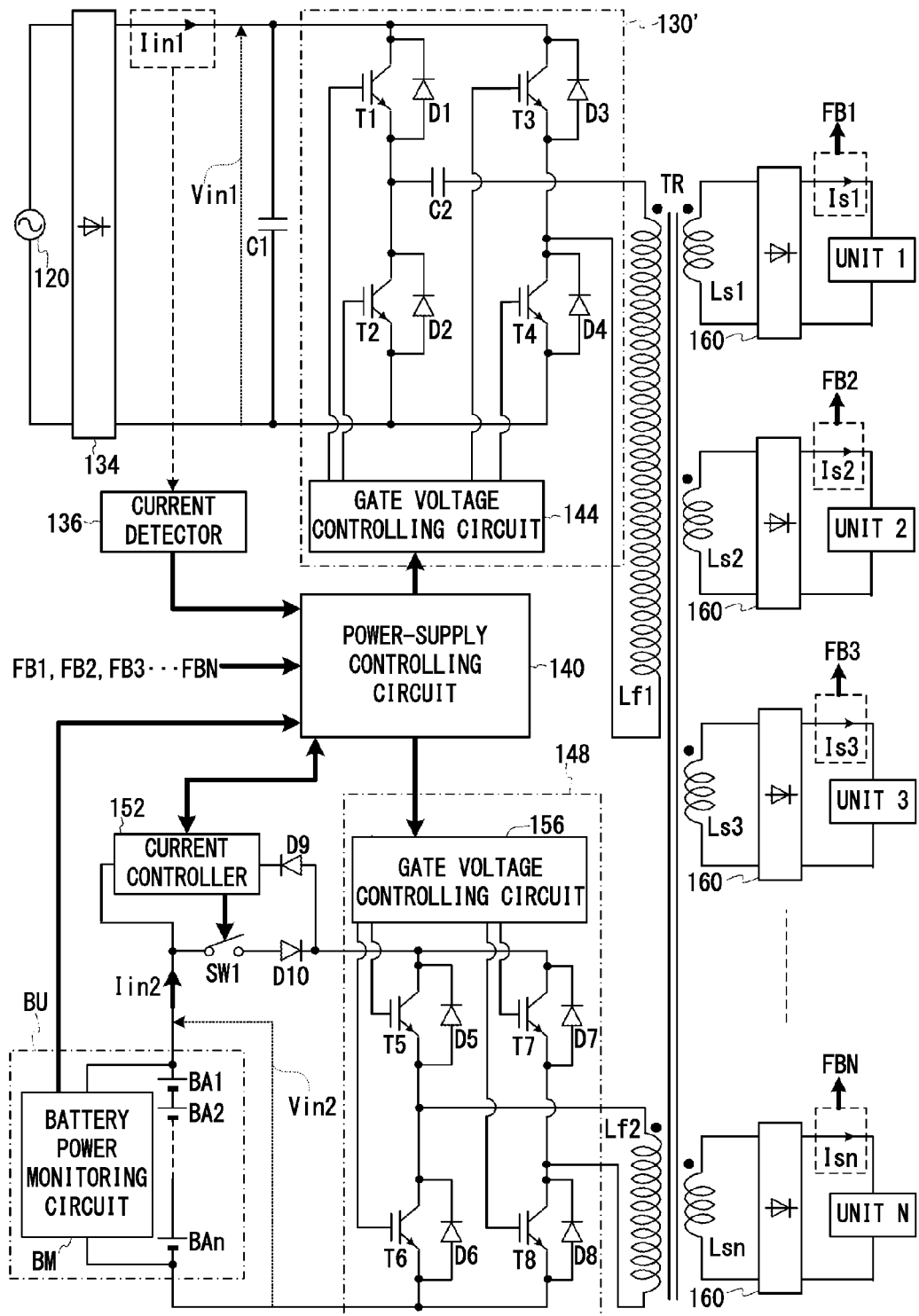
FIG. 9 is a schematic circuit diagram of a modified example of the electric power supply system of the MRI apparatus of the first embodiment.

[3] FIG. 9 is a schematic circuit diagram of a modified example of the electric power supply system of the MRI apparatus 20 of the first embodiment. As shown in FIG. 9, in the first switching circuit 130', a capacitor C2 may be inserted in series between the first primary winding Lf1 and the connection node between the transistor T1 and the transistor T2 (this point applies to the second to the fourth embodiments). In the modified embodiment of FIG. 9, other parts are the same as the circuit structure explained with FIG. 3.

In the modified example of FIG. 9, flowing too much of electric current in each of the transistors T1 to T4 in the first switching circuit 130' can be prevented by the capacitor C2. In a normal use state of the MRI apparatus 20, one cycle of switching is kept sufficiently short, and thus the application voltage to the capacitor C2 is approximately close to the alternate current. That is, because the frequency is so large that the impedance of the capacitor C2 is substantively negligible, the circuit operation in the modified example of FIG. 9 is similar to that of the aforementioned FIG. 3.

The Second Embodiment

Figure 10:
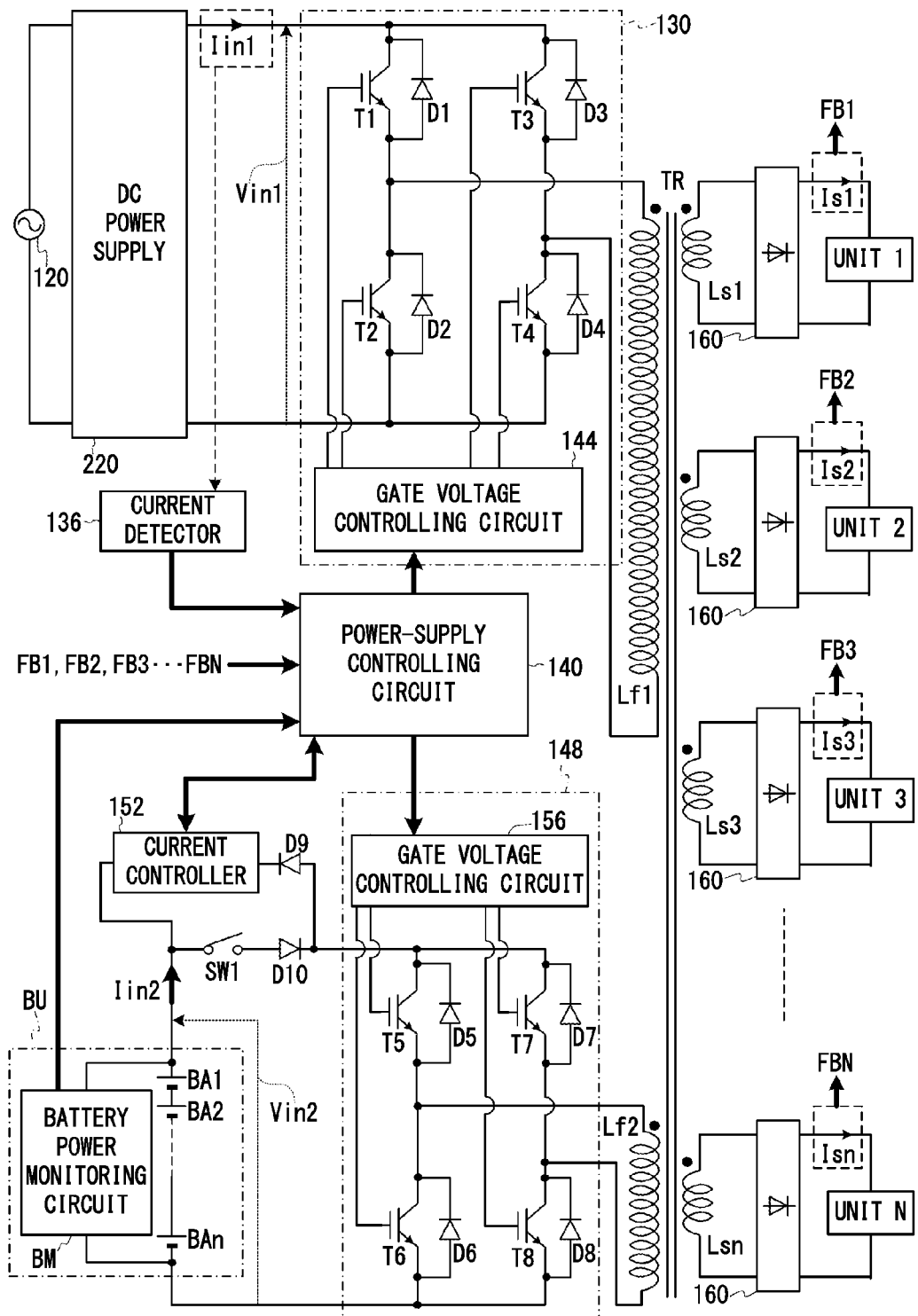
FIG. 10 is a schematic circuit diagram of the electric power supply system of the MRI apparatus of the second embodiment.

FIG. 10 is a schematic circuit diagram of the electric power supply system of the MRI apparatus 20 of the second embodiment. Because the structure of the imaging system of the MRI apparatus 20 of the second embodiment to the fourth embodiment is the same as the first embodiment explained with FIG. 2, its explanation is omitted. The second embodiment is an embodiment in which a part of the power supply system of the first embodiment is changed in order to ensure that the battery unit BU is charged.

As the aforementioned equation (4), in order to charge the battery unit BU, it is desired to satisfy the electrifiable condition of (Vin2$m$/Tf2)<(Vin1/Tf1). By designing each component in accordance with the external power source 120 as input, the structure of the first embodiment sufficiently functions for practical use. On the other hand, the frequency and amplitude of the input of the external power source 120 differ per country, because it is, for example, a commercial power source. There is a possibility that the battery unit BU cannot be sufficiently charged, in the unlikely event of declining the primary side voltage Vin1 too much by variation in the primary side voltage Vin1 caused by the above voltage variation.

Then, in the second embodiment, as shown in FIG. 10, the DC power supply 220 is disposed in the rear stage of the external power source 120, instead of the smoothing capacitor C1 and the rectifier 134 in FIG. 3. The DC power supply 220 is a constant-voltage source which receives the alternating external electric power from the external power source 120 and converts it into direct current. The DC power supply 220 fixes the value of the primary side voltage Vin1.

The circuit operation of the power supply system of the MRI apparatus 20 in the second embodiment is the same as the first embodiment including the charging mode, the discharging mode and the standby mode, except that the primary side voltage Vin1 is fixed.

In addition, the imaging operation of the MRI apparatus 20 of the second embodiment is the same as the flow explained in FIG. 8 and what is explained in the supplementary notes of the first embodiment.

As just described, in the second embodiment, the same effect as the first embodiment can be obtained. Moreover, in the second embodiment, because the primary side voltage Vin1 is stabilize at a constant voltage, the battery unit BU can be charged sufficiently and unfailingly regardless of the voltage variation of the external power source 120.

The Third Embodiment

Figure 11:
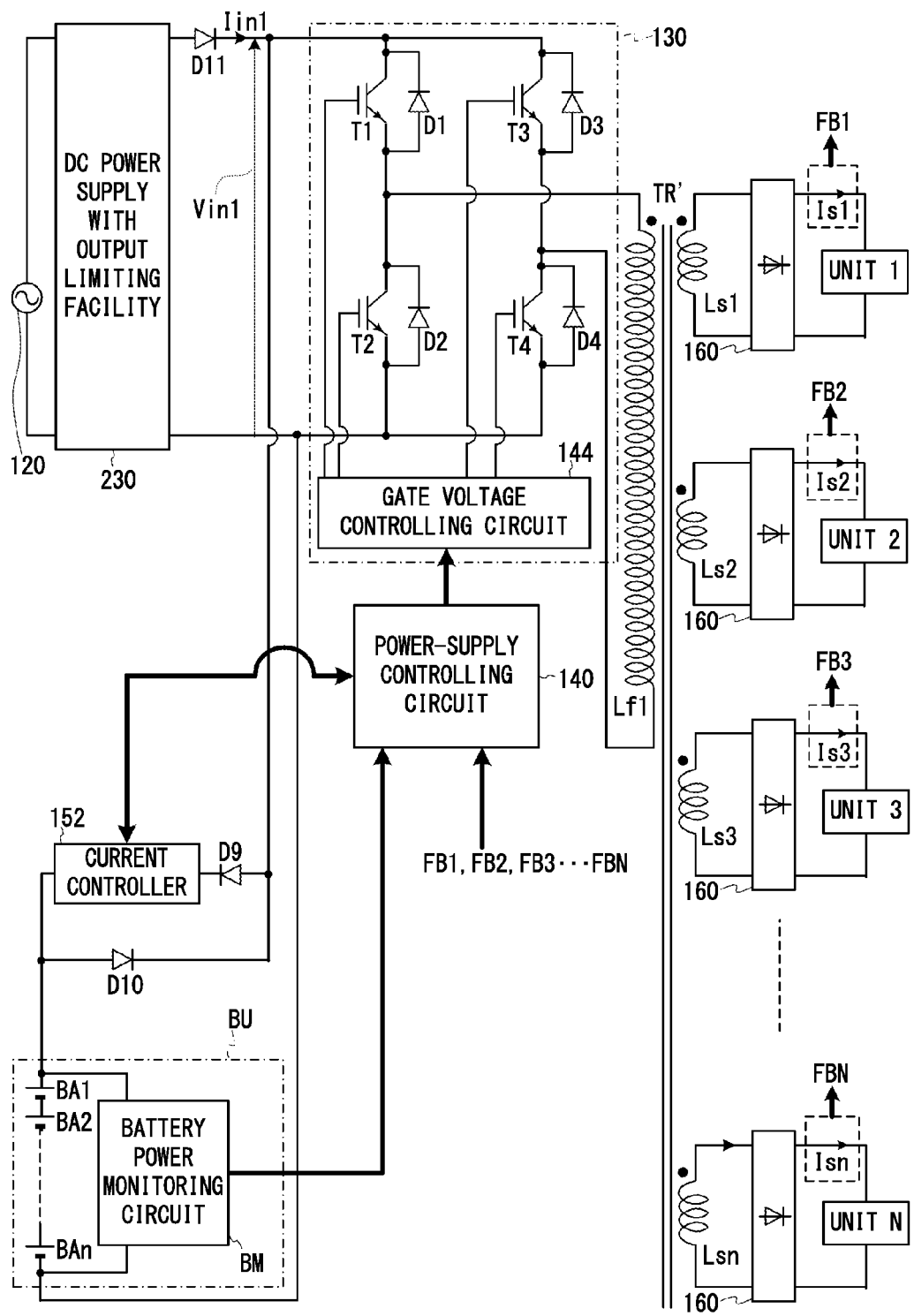
FIG. 11 is a schematic circuit diagram of the electric power supply system of the MRI apparatus of the third embodiment.

FIG. 11 is a schematic circuit diagram of the electric power supply system of the MRI apparatus 20 of the third embodiment. The third embodiment is an embodiment whose circuit structure is simplified by unifying the winding of the primary side of the second embodiment. Firstly, the circuit structure will be explained by focusing on the difference between the second embodiment and the present embodiment.

As shown in FIG. 11, the transformer TR' in the third embodiment is the same as the transformer TR of the second embodiment shown in FIG. 10, except that the second primary winding Lf2 is omitted. The (first) primary winding Lf1 is magnetically coupled to each of the secondary windings Ls1 to Lsn, respectively.

In addition, in the third embodiment, the DC power supply 220, the current detector 136, the switch SW1 and the second switching circuit 148 of the second embodiment are omitted, and alternatively, a direct-current power source 230 with output limiting facility and a diode D11 are disposed. The diode D11 prevents the discharging current from the battery unit BU from flowing into the side of the direct-current power source 230 with output limiting facility.

Figure 12:
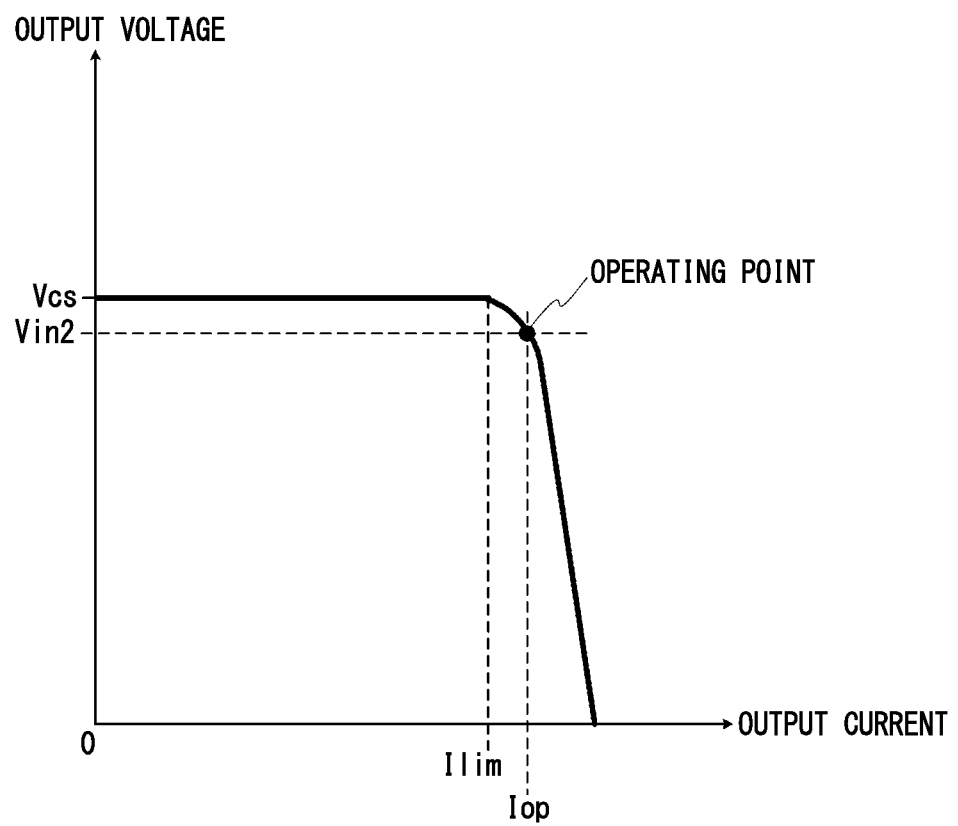
FIG. 12 is a schematic diagram showing characteristics of an output voltage and an output current of "a direct-current power source with output limiting facility" in the third embodiment.

FIG. 12 is a schematic diagram showing characteristics of an output voltage and an output current of the direct-current power source 230 with output limiting facility in the third embodiment. As shown with a bold line in FIG. 12, the output voltage of the direct-current power source 230 with output limiting facility is constant at a predetermined voltage (in this example, the rated voltage Vcs) until its output current reaches the rated current value Him. However, the output voltage gradually declines from the rated voltage Vcs, when the output current exceeds the rated current value Him in association with the increase of the consumed power on the secondary side.

Note that, the rated voltage Vcs of the direct-current power source 230 with output limiting facility is higher than the charging voltage Vin2$m$ of the battery unit BU at completion of charging by the voltage drop in the current controller 152 and the diode D9. This is so that the battery unit BU can be sufficiently charged up to the charging voltage Vin2$m$ at completion of charging. Thus, in order for the battery unit BU not to be charged on a steady basis, inflow of the charging current to the battery unit BU is restricted by the current controller 152 and the diode D10.

By disposing the above direct-current power source 230 with output limiting facility, the circuit operation of the power supply system of the MRI apparatus 20 in the third embodiment becomes as follows.

Firstly, in FIG. 12, the point at which the output voltage of the direct-current power source 230 with output limiting facility becomes the charging voltage of the battery unit BU Vin2 is defined as the operating point, and the output current of the direct-current power source 230 with output limiting facility at this operating point is defined as Iop.

When the consumed power on the secondary side increases and the output current of the direct-current power source 230 with output limiting facility increases, the direct-current power source 230 with output limiting facility continues to output the constant rated voltage Vcs until the output current thereof reaches the rated current value Ilim. When the consumed power on the secondary side further increases and the output current value of the direct-current power source 230 with output limiting facility exceeds the rated current value Ilim, the output voltage of the direct-current power source 230 with output limiting facility starts to gradually fall from the rated voltage Vcs, and it falls to the charging voltage of the battery unit BU Vin2.

However, the output voltage of the direct-current power source 230 with output limiting facility never falls below the charging voltage Vin2 of the battery unit BU. This is because, even if the direct-current power source 230 with output limiting facility operates so as to increase its output current and the output voltage further declines, the charging voltage Vin2 of the battery unit BU becomes higher than the output voltage of the direct-current power source 230 with output limiting facility and accordingly the discharging current of the battery unit BU flows into the first primary winding Lf1. At this time, because the diode D11 is disposed, the discharging current of the battery unit BU never flows into the side of the direct-current power source 230 with output limiting facility.

Therefore, when the excitation current flowing the primary winding Lf1 of the transformer TR' increases over Iop in association with the increase in the consumed power on the secondary side, the amount up to Iop is supplied from the direct-current power source 230 with output limiting facility and the excess amount beyond Iop is supplied by the discharging current of the battery unit BU. Thus, in the discharging mode, the direct-current power source 230 with output limiting facility operates at the operating point of FIG. 11 at which the output voltage of the direct-current power source 230 with output limiting facility is equal to the charging voltage Vin2 of the battery unit BU.

In other words, the total voltage of the charging voltage Vin2 of the battery unit BU and the voltage drop in the current controller 152 and the diode D10 becomes higher than the output voltage of the direct-current power source 230 with output limiting facility even slightly, the battery unit BU automatically discharges via the diode D10.

That is, though switching from the standby mode to the discharging mode is automatically controlled by the current controller 152, the switch SW1 and the power-supply controlling circuit 140 in the first embodiment and the second embodiment, it is automatically switched without control of the power-supply controlling circuit 140 and so on in the third embodiment.

In addition, when the output voltage of the direct-current power source 230 with output limiting facility is higher than the total voltage of the charging voltage Vin2 of the battery unit BU and the voltage drop in the current controller 152 and the diode D10, the charging current flows into the battery unit BU from the direct-current power source 230 with output limiting facility via the diode D9 and the current controller 152.

That is, though switching from the discharging mode or the standby mode to the charging mode is automatically controlled by the power-supply controlling circuit 140 or the like in the first embodiment and the second embodiment, it is automatically switched without control of the power-supply controlling circuit 140 or the like in the third embodiment.

At this time, the power-supply controlling circuit 140 controls the amplitude of the charging current flowing into the battery unit BU by controlling the length of the conductive period of the current controller 152, in the way similar to the charging mode in the first embodiment (see FIG. 6).

Then, when the charging voltage Vin2 of the battery unit BU reaches the voltage Vin2$m$ at completion of charging, the total voltage of the voltage Vin2$m$ and the voltage drop in the current controller 152 and the diode D9 becomes equal to the rated voltage Vcs of the direct-current power source 230 with output limiting facility. Thereby, inflow of the charging current from the direct-current power source 230 with output limiting facility to the battery unit BU stops. That is, the switching from the charging mode to the standby mode is automatically performed, too.

As just described, because the switching between the discharging mode, the standby mode and the charging mode is automatically performed except the control of the length of the conductive state of the current controller 152 in the charging mode, the current detector 136, the switch SW1 and the second switching circuit 148 in the second embodiment can be omitted.

In addition, the power-supply controlling circuit 140 inputs the control information such as length of the on-span, length of off-span, length of the dead time and so on to the gate voltage controlling circuit 144, in accordance with the feedback signals FB1 to FBN and the conditions of the imaging sequence in the way similar to the first embodiment and the second embodiment. The gate voltage controlling circuit 144 outputs the respective gate voltages of the transistors T1 to T4 on the basis of this control information. As just described, the consumed power on the secondary side is controlled by the duty ratio. The foregoing is the explanation of the circuit operation of the power supply system of the MRI apparatus 20 in the third embodiment.

In addition, the imaging operation of the MRI apparatus 20 of the third embodiment is the same as the flow explained with FIG. 8 and what is explained in the supplementary notes of the first embodiment, except the switching of the three operation states of the battery unit BU.

As just described, in the third embodiment, the same effects as the second embodiment can be obtained. Moreover, in the third embodiment, the switching between the discharging mode, the standby mode and the charging mode is automatically performed without control of the power-supply controlling circuit 140 and so on, by disposing the direct-current power source 230 with output limiting facility. Therefore, the second switching circuit 148 can be omitted and the primary side winding of the transformer TR' can be single. Thus, circuit structure of the power supply system can be simplified. As a result, the consumed power of the power supply system can be reduced and a power-supply facility can be further downsized.

The Fourth Embodiment

Figure 13:
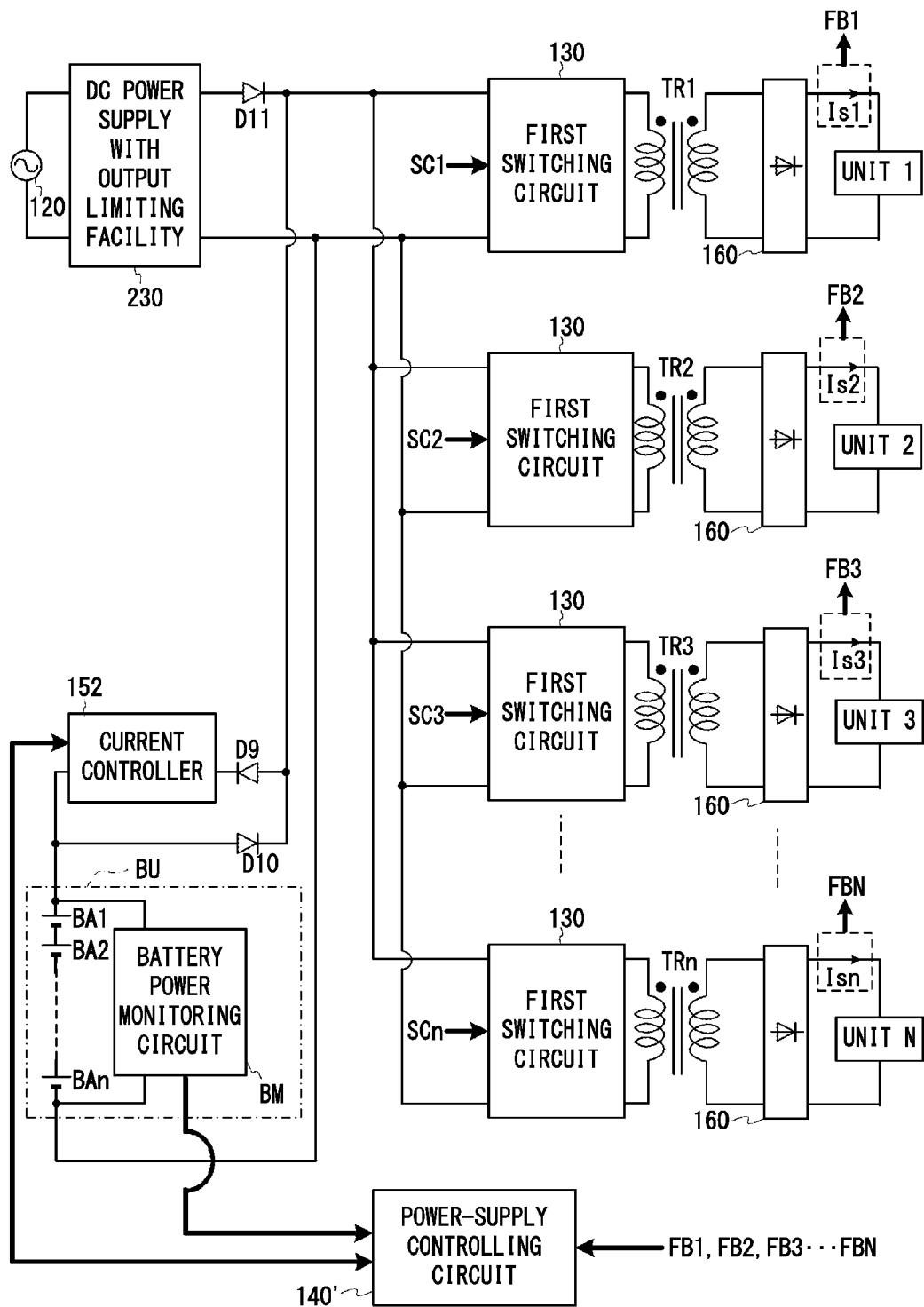
FIG. 13 is a schematic circuit diagram of the electric power supply system of the MRI apparatus of the fourth embodiment.

FIG. 13 is a schematic circuit diagram of the electric power supply system of the MRI apparatus 20 of the fourth embodiment. The fourth embodiment corresponds to a subordinate concept of the third embodiment. An example in which the electric power of all the units 1 to N of the imaging system is distributed by one transformer TR' has been explained in the third embodiment, but this is only an example.

For example, the first transformer may distribute electric power to a plurality of units on the secondary side, the second transformer may distribute electric power to another plurality of units on the secondary side, and the third transformer may distribute electric power to all the rest of units on the secondary side (not shown).

Alternatively, like the fourth embodiment shown in FIG. 13, the first transformer TR1, the second transformer TR2, the third transformer TR3, . . . and the N-th transformer TRn may be respectively disposed for the units 1 to N.

In FIG. 13, each of the first transformer TR1 to the N-th transformer TRn includes a primary winding and a secondary winding mutually magnetically coupled with homopolarity. Note that, the magnetic coupling of windings may be reversed polarity. The first switching circuit 130 which is the same as the first embodiment is connected to the primary side of each of the first transformer TR1 to the N-th transformer TRn. The rectifier 160 is connected to the secondary side of each of the first transformer TR1 to the N-th transformer TRn. In the secondary side, each of the units 1 to N is connected to the rear stage of the rectifier 160 and supplied with direct-current power.

In the fourth embodiment, the consumed power on the secondary side is controlled by separate duty ratios per each of the units 1 to N. More specifically, the power-supply controlling circuit 140' of the fourth embodiment calculates the control information such as length of the on-span, length of the off-span, length of the dead time and so on per each of the units 1 to N, in accordance with the conditions of the imaging sequence and the feedback signals FB1 to FBN inputted from each of the units 1 to N.

The power-supply controlling circuit 140' inputs the calculated control information as the gate voltage control signals SC1, SC2, SC, . . . and SCn into the gate voltage controlling circuit 144 (see FIG. 3) of each of the first switching circuit 130.

Then, each of the gate voltage controlling circuit 144 outputs the respective gate voltages of the transistors T1 to T4 on the basis of the gate voltage control signals SC1 to SCn. The switching of the operation states of the battery unit BU between the charging mode, the discharging mode and the standby mode is the same as the third embodiment. The forgoing is the explanation of the circuit operation of the power supply system of the MRI apparatus 20 in the fourth embodiment.

In addition, the imaging operation of the MRI apparatus 20 in the fourth embodiment is the same as the flow explained with FIG. 8 and what is explained in the supplementary notes of the first embodiment, except the switching of the three operation states of the battery unit BU.

As just described, in the fourth embodiment, the same effects as the third embodiment can be obtained. Moreover, in the fourth embodiment, by taking advantage of eliminating the need for intervention of a transformer in discharge and charge of the battery unit BU in the third embodiment, the transformers are separated and accordingly supplied power on the secondary side can be separately adjusted per each of the units 1 to N.

<Supplementary Notes on First to Fourth Embodiments>

[1] In the first embodiment to the fourth embodiment, an example in which alternating electric power supplied from the external power source 120 to the primary side via the transformer is subjected to AC/AC conversion and then direct-current power is supplied to each of the units 1 to N on the secondary side has been explained. As shown in the following FIG. 14 to FIG. 16, embodiments of the present invention are not limited to such an aspect.

Figure 14:
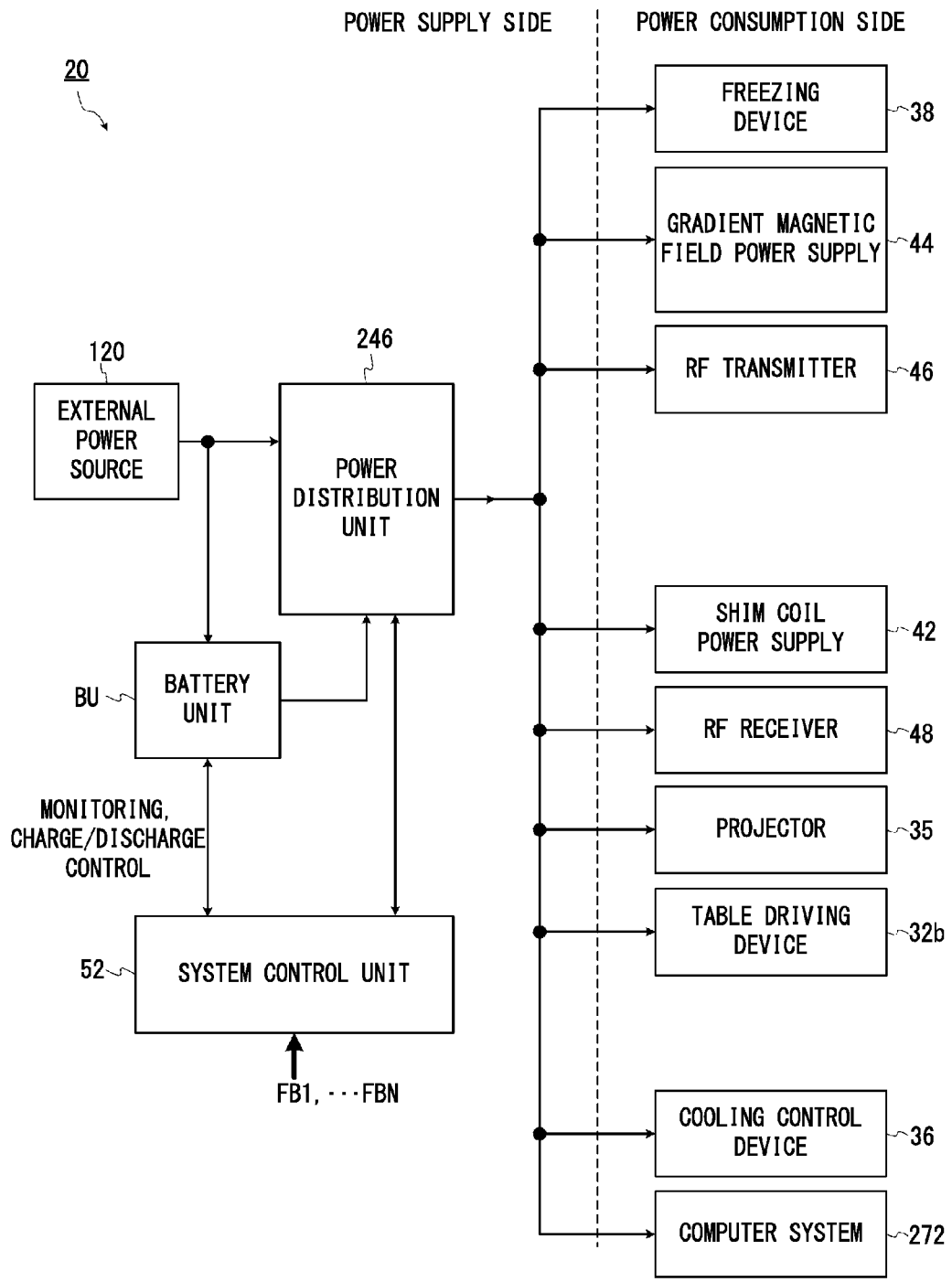
FIG. 14 is a block diagram showing a concept of supplying electric power of the MRI apparatuses of the first embodiment to the fourth embodiment.

FIG. 14 is a block diagram showing a concept of supplying electric power of the MRI apparatuses 20 of the first to the fourth embodiments. In FIG. 14, the left side of the separating dashed line is the power supply side, and corresponds to the primary side of the first embodiment to the fourth embodiment. The power supply side is a hybrid type structure whose electric power sources are the external electric power supplied from the external power source 120 and the charge/discharge element (in this example, the battery unit BU) which is charged with the external electric power and compensates electric power at the time of need.

Note that, though the system control unit 52 is disposed to the power supply side as a matter of practical convenience in FIG. 14, the system control unit 52 functions as not only an element of control of power supply but also an element of power consumption side. More specifically, the system control unit 52 performs control of imaging operation and so on by using electric power.

On the other hand, the right side of the dividing dashed line in the vertical direction is the power consumption side, and they correspond to the respective components shown in the block diagram of the MRI apparatus in FIG. 2. The computer system 272 in FIG. 14 corresponds to, for example, the image reconstruction unit 56, the image database 58, the image processing unit 60, the input device 62, the display device 64 and the storage device 66 in FIG. 2. The power consumption side in FIG. 14 corresponds to each of the units 1 to N of the secondary side of the first embodiment to the fourth embodiment.

Here, the MRI apparatus 20 of each embodiment is not limited to an aspect of distributing electric power via a transformer. For example, electric power may be directly distributed to at least one or some units from the external power source 120 (see later-described FIG. 15). Thus, the power distribution unit in FIG. 14 may be configured to perform distribution with a transformer like the first embodiment to the fourth embodiment, or may be configured to perform direct distribution, for example.

Figure 15:
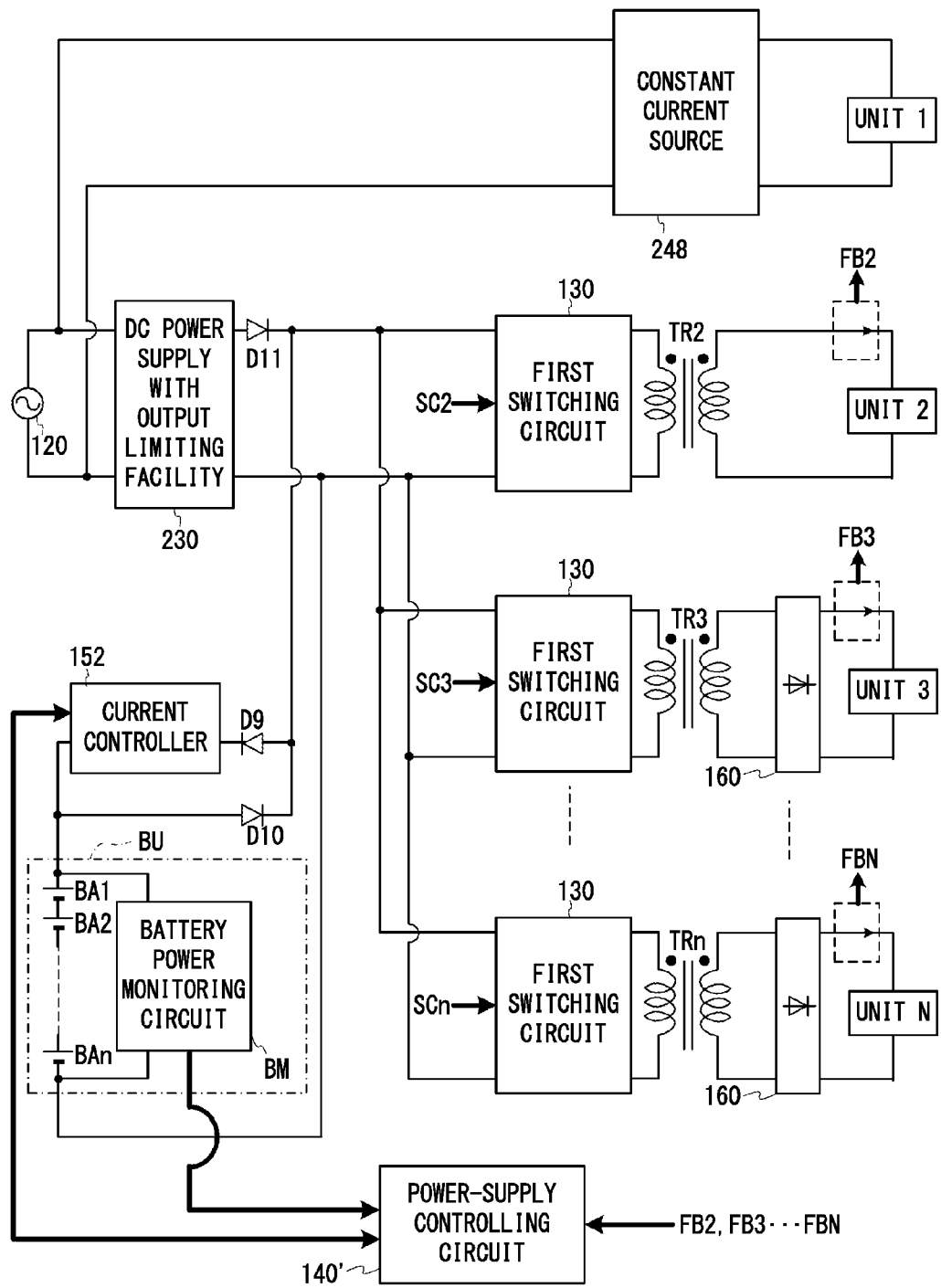
FIG. 15 is a schematic circuit diagram of the first modified example of the electric power supply system of the MRI apparatus of the fourth embodiment.

FIG. 15 is a schematic circuit diagram of the first modified example of the electric power supply system of the MRI apparatus 20 of the fourth embodiment. In the structure of FIG. 15, electric power is directly distributed to the unit 1 from the external power source 120 via a constant current source 248 without going through a transformer and the direct-current power source 230 with output limiting facility.

In addition, because the rectifier 160 is not disposed to the secondary side of the transformer TR2, as to the unit 2, alternating electric power from the external power source 120 is subjected to AC/AC conversion and then supplied to the unit 2.

Figure 16:
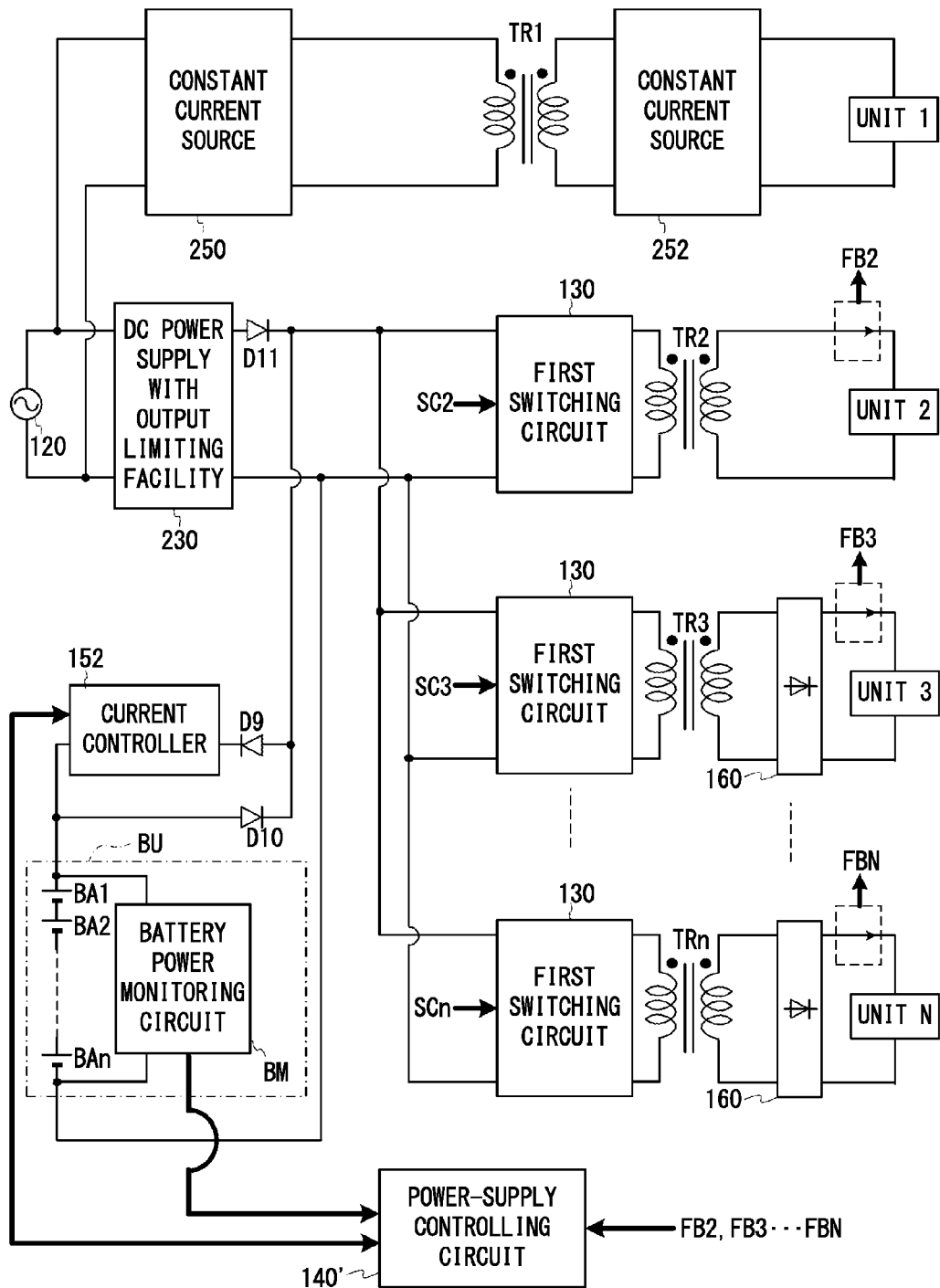
FIG. 16 is a schematic circuit diagram of the second modified example of the electric power supply system of the MRI apparatus of the fourth embodiment.

FIG. 16 is a schematic circuit diagram of the second modified example of the electric power supply system of the MRI apparatus 20 of the fourth embodiment. In the structure of FIG. 16, the electric power is directly distributed to the unit 1 from the external power source 120 via the transformer TR1 without going through the direct-current power source 230 with output limiting facility.

As an example in FIG. 16, a constant current source 250 supplies a constant electric current of direct-current to the primary winding of the transformer TR1 as the excitation current. Thereby, the induced current is caused in the secondary winding of the transformer TR1 and this induced current is supplied to the unit 1 as a constant electric current of direct-current by a constant current source 252. Note that, as components consuming an approximately constant electric power regardless of time like this unit 1, for example, the freezing device 38 and so on are included. Other structures are the same as the first modified example shown in FIG. 15.

[2] When electric power supply from the external power source 120 stops during operating period of the MRI apparatus 20 (power-on period) by, for example, electric power failure, the power supply system may be switched to the discharging mode so as to make the MRI apparatus 20 operate by the accumulated power of the battery unit BU. In this case, it is preferable that the system control unit 52 judges whether the imaging sequence can be performed through to completion or not on the basis of the charging voltage Vin2 of the battery unit BU and then switch the operation state of the MRI apparatus 20 in accordance with the judgment result.

That is, if the imaging sequence can be performed through to completion, the system control unit 52 may switch to the discharging mode so as to perform the imaging sequence through to completion and safely stop the operation of the MRI apparatus 20 under the state where the k-space data are stored. On the other hand, if the imaging sequence cannot be performed through to completion, the system control unit 52 may safely discontinue the imaging sequence and safely stop the operation of the MRI apparatus 20.

[3] As the MRI apparatus 20, an example in which the RF receiver 48 is disposed outside the gantry 21 has been described (see FIG. 2). However, embodiments of the preset invention are not limited to such an aspect. The RF receiver 48 may be included in the gantry 21.

Specifically, for example, an electronic circuit board that is equivalent to the RF receiver 48 may be disposed in the gantry 21. Then, the MR signals, which are analog electrical signals converted from the electromagnetic waves by the reception RF coil 29 and the wearable RF coil device 100, may be amplified by a preamplifier in the electronic circuit board, the amplified signals may be outputted to the outside of the gantry 21 as digital signals and inputted to the image reconstruction unit 56. In outputting the signals to the outside of the gantry 21, for example, an optical communication cable is preferably used to transmit the signals in the form of optical digital signals. This is because the effect of external noise is reduced.

[4] Examples in which the novel technology of hybrid-type power control is applied to the MRI apparatuses have been explained in the first embodiment to the fourth embodiment as examples of image diagnosis apparatuses. However, embodiments of the present invention are not limited to such an aspect. The aforementioned novel technology of hybrid-type power control can be applied to other image diagnosis apparatuses whose power consumption is large such as an X-ray diagnostic apparatus and an X-ray computed tomography apparatus.

Note that, an X-ray diagnostic apparatus is an apparatus which detects X-rays penetrating an object with, for example, a plurality of detection elements arranged in a matrix, and generates image data in such a manner that each pixel indicates luminance in accordance with detection amount of X-rays of each detection element.

Figure 17:
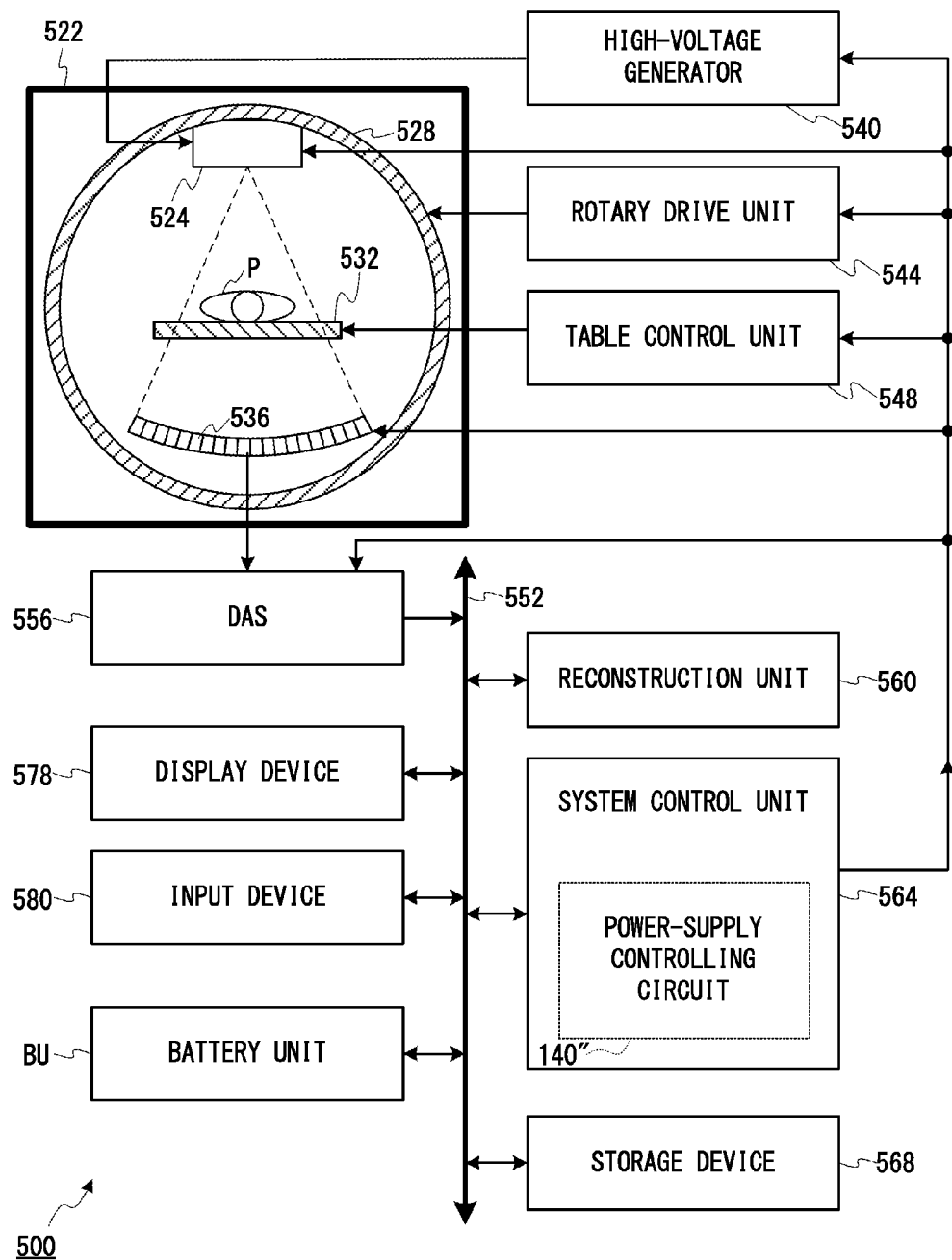
FIG. 17 is a block diagram showing an example of general structure of an X-ray CT apparatus to which the novel technology of hybrid-type power control is applied.

FIG. 17 is a block diagram showing an example of a general structure of an X-ray CT apparatus 500 to which the aforementioned novel technology of the hybrid-type power control is applied.

As shown in FIG. 17, the X-ray CT apparatus 500 includes a gantry 522, an X-ray tube 524, a rotary unit 528, a table 532, an X-ray detector 536, a high-voltage generator 540, a rotary drive unit 544, a table control unit 548, a system bus 552, a DAS (Data Acquisition System) 556, a reconstruction unit 560, a system control unit 564, a storage device 568, a display device 578, an input device 580 and a battery unit BU.

The X-ray CT apparatus 500 is a hybrid-type that operates with the use of the external power source 120 (not shown in FIG. 17) and the rechargeable batteries inside the battery unit BU.

In the following, functions of the respective units will be explained.

The gantry 522 rotatably supports the rotary unit 528 which is in the form of a circle or a disc.

The table 532 is inserted into an opening section (not shown) formed in the center part of the rotary unit 528, and the object P is loaded on the table 532.

Inside the rotary unit 528, the radiation aperture of the X-ray tube 524 and the X-ray detector 536 are arranged so as to face each other with the object P positioned between them.

The X-ray detector 536 is a structure of arranging multi-channel detection elements in the form of an arc, and detects X-rays that are emitted from the X-ray tube 524 and penetrates the object P.

The rotary drive unit 544 drives the rotary unit 528 on the basis of drive control signal inputted from the system control unit 564, so as to continuously rotate the X-ray tube 524 and the X-ray detector 536 supported by the rotary unit 528 around the object P.

The table control unit 548 controls the position of the table 532 on the basis of a table control signal inputted from the system control unit 564.

The high-voltage generator 540 is connected to a high voltage cable of the X-ray tube 524. The high-voltage generator 540 supplies the X-ray tube 524 with predetermined tube current and tube voltage, on the basis of an X-ray control signal supplied from the system control unit 564.

The system control unit 564 set radiographic conditions in accordance with conditions inputted to the input device 580, and controls each component of the X-ray CT apparatus 500.

In addition, the system control unit 564 is connected to a control unit (not shown) of the X-ray tube 524, and controls radiography with the use of X-rays irradiated from the X-ray tube 524.

In addition, the system control unit 564 includes a power-supply controlling circuit 140 that functions in the same way as the power-supply controlling circuit 140 in the first embodiment or the power-supply controlling circuit 140' in the third embodiment, and controls the electric power system of the X-ray CT apparatus 500.

The DAS 556 collects projection data reflecting an X-ray transmission factor per X-ray path detected by the X-ray detector 536 on the basis of a data collection control signal inputted from the system control unit 564, and inputs the projection data into the reconstruction unit 560 and the storage device 568.

The reconstruction unit 560 performs reconstruction processing on the projection data collected for a plurality of slice planes of the object P, and generate image data of the object P.

The storage device 568 stores the projection data collected for a plurality of slice planes of the object P. In addition, the storage device 568 stores the image data generated by the reconstruction unit 560.

The input device 580 includes input devices such as a keyboard, and inputs information on the object P and radiographic conditions inputted by an operator to the system control unit 564.

The display device 578 displays images of the object P on the basis of the image data generated by the reconstruction unit 560.

In the case of the MRI apparatus 20, the unit that consumes especially large amount of consumed power in time of imaging as compared with other units is the gradient magnetic field power supply 44, and the next one is the RF transmitter 46.

On the other hand, in the case of the X-ray CT apparatus 500, the units which consume especially large amount of consumed power in time of radiography as compared with other units are the high-voltage generator 540 and the X-ray tube 524 generating X-rays with the use of high voltage supplied from the high-voltage generator 540.

As to the power control of the above X-ray CT apparatus 500, a power control circuit similar to FIG. 3 may be included in the X-ray CT apparatus 500. In this case, feedback signals indicative of the current consumed power are respectively inputted from each unit of the X-ray tube 524, the rotary unit 528, the X-ray detector 536, the high-voltage generator 540, the rotary drive unit 544, the table control unit 548, the DAS 556 and so on to the system control unit 564. Thereby, the system control unit 564 switches it to one of the charging mode, the discharging mode and the standby mode in accordance with the consumed power of the entirety of the X-ray CT apparatus 500, in the way similar to the first embodiment.

Alternatively, a power control circuit similar to FIG. 11 or a power control circuit similar to FIG. 13 may be included in the X-ray CT apparatus 500 so that switching between the discharging mode, the standby mode and the charging mode are automatically performed in the way similar to the third embodiment and the fourth embodiment. In this case, the unit 1 in FIG. 11 and FIG. 13 corresponds to, for example, the high-voltage generator 540, the unit 2 corresponds to, for example, the rotary drive unit 544, and the unit 3 corresponds to, for example, the X-ray detector 536.

The X-ray CT apparatus 500 operates with the use of the accumulated power of the battery unit BU and the external electric power in implementation term of radiography whose consumed power is large under the aforementioned power control, and can operate with the use of only the external electric power in other cases. In this structure, the maximum value of the external electric power supplied from the external electric power can be reduced by the amount of the accumulated power of the battery unit BU without decreasing the maximum consumed power. That is, the same effects as the first embodiment to the fourth embodiment can be obtained.

[5] In the following, correspondences between terms used in the claims and terms used in the embodiment described will be described. Note that the correspondences described below are just some of possible interpretations for reference and should not be construed as limiting the present invention.

Each of the data collecting system, i.e. (1) the static magnetic field magnet that generates a static magnetic field, (2) the shim coil 24 and the shim coil power supply 42 that uniform the static magnetic field, (3) the gradient magnetic field coil 26 and the gradient magnetic field power supply 44 that apply gradient magnetic fields, (4) the transmission RF coil 28 and the RF transmitter 46 that transmit RF pulses to the object P, (5) the reception RF coil 29 and the RF receiver 48 that receive MR signals and (6) the system control unit 52 is an example of the imaging unit described in the claims.

The data processing system that includes the image reconstruction unit 56, the image database 58, the image processing unit 60 and so on is an example of the imaging unit described in the claims.

The period during which the consumed power is larger than the external electric power is an example of a period during which the consumed power is larger than a predetermined power amount described in the claims. This predetermined power amount may be the maximum power amount available from the external power source 120, or it may be lower than the maximum power amount available from the external power source 120 by a prescribed margin.

The function of the diodes D9 and D10, the current controller 152 and the power-supply controlling circuit 140 that control discharge and charge of the battery unit BU by switching the power supply system of the MRI apparatus 20 to one of the charging mode, the discharging mode and the standby mode is an example of the charge/discharge control circuit described in the claims.

The function of the system control unit 52 that judges whether the imaging sequence is practicable or not on the basis of the estimated time variation of the consumed power is an example of the judging unit described in the claims.

The gantry 522, the X-ray tube 524, the rotary unit 528, the table 532, the X-ray detector 536, the high-voltage generator 540, the rotary drive unit 544, the table control unit 548, the system bus 552, DAS 556, the reconstruction unit 560 and the system control unit 564 in the X-ray CT apparatus 500 are examples of the computed tomography structure descried in the claims.

[6] While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An image diagnosis apparatus generating image data of an object by using external electric power supplied from an external power source, comprising:
 a magnetic resonance imaging (MRI) system configured to consume external electric power supplied from an external power source while generating MRI data of an object, the MRI system including a plurality of power consuming units, each power consuming unit being configured to perform respectively corresponding different imaging operations during an MRI procedure that generates said MRI data;
 a battery configured to be charged with the external electric power and to be subsequently discharged while supplying a part of the MRI system consumed power;
 a charge/discharge control circuit configured to control charge and discharge of the battery in such a manner that (a) the consumed power is supplied by the battery and the external power source in a period during which the consumed power is larger than a predetermined power amount and (b) the battery is charged in a period during which the consumed power is smaller than the predetermined power amount; and
 a voltage converter configured to convert electric power voltage supplied from at least one of the external power source and the battery such that arbitrary voltages are respectively supplied to the plurality of power consuming units.

2. The image diagnosis apparatus according to claim 1, wherein the charge/discharge control circuit is configured to charge the battery with the external electric power if the consumed power is smaller than the external electric power and a charging voltage of the battery is below a voltage at completion of charging while an MRI sequence is being performed.

3. The image diagnosis apparatus according to claim 2, further comprising:
 a transformer including a first primary winding, a second primary winding and a secondary winding that are magnetically coupled to each other;
 a rectifier configured to receive the external electric power, convert the external electric power into direct-current power and output the direct-current power;
 a first switching circuit configured to cause an alternating excitation current to flow in the first primary winding and generate induced currents in the second primary winding and the secondary winding, by performing periodic switching on the direct-current power; and
 a second switching circuit configured to cause an alternating excitation current to flow in the second primary winding and generate induced currents in the secondary winding by performing periodic switching on a discharging current, when the discharging current is outputted from the battery,
 wherein the battery is charged according to an induced voltage generated in the second primary winding.

4. The image diagnosis apparatus according to claim 3, further comprising a battery power monitoring circuit configured to detect the charging voltage of the battery and input the charging voltage to the charge/discharge control circuit,
 wherein the MRI system includes a plurality of power consuming units configured to respectively receive the induced currents flowing in the secondary winding, perform a complete MRI sequence, and respectively output a plurality of feedback signals as indices of consumed power on a secondary side; and
 the charge/discharge control circuit is configured to switch to one of a state of charging the battery, a state of discharging the battery and a state in which charge or discharge is not performed, according to the charging voltage and the plurality of feedback signals.

5. The image diagnosis apparatus according to claim 4, wherein the charge/discharge control circuit is configured to control charge and discharge of the battery in such a manner that the battery is charged in an implementation term of an MRI sequence whose consumed power amount is estimated to be equal to or lower than a predetermined value and the battery is not charged in an implementation term of an MRI sequence whose consumed power amount is estimated to exceed the predetermined value.

6. The image diagnosis apparatus according to claim 2, further comprising:
 a transformer including a first primary winding, a second primary winding and a secondary winding that are magnetically coupled to each other;
 a direct-current power source configured to receive the external electric power, convert the external electric power into direct-current power of a constant voltage, and output the direct-current power;
 a first switching circuit configured to cause an alternating excitation current to flow in the first primary winding and generate induced currents in the second primary winding and the secondary winding, by performing periodic switching on the direct-current power; and
 a second switching circuit configured to cause an alternating excitation current to flow in the second primary winding and generate induced currents in the secondary winding by performing periodic switching on a discharging current, when discharging current is outputted from the battery,
 wherein the battery is charged according to an induced voltage generated in the second primary winding.

7. The image diagnosis apparatus according to claim 6, further comprising a monitoring circuit configured to detect the charging voltage of the battery and input the charging voltage to the charge/discharge control circuit,
 wherein the MRI system includes a plurality of power consuming units configured to respectively receive the induced currents flowing in the secondary winding, perform magnetic resonance imaging as a whole, and respectively output a plurality of feedback signals as indices of consumed power on a secondary side; and
 the charge/discharge control circuit is configured to switch to one of a state of charging the battery, a state of discharging the battery and a state in which charge or discharge is not performed, according to the charging voltage and the plurality of feedback signals.

8. The image diagnosis apparatus according to claim 2, further comprising:
a transformer including a primary winding and a secondary winding that are magnetically coupled to each other;
a direct-current power source configured to receive the external electric power, convert the external electric power into direct-current electricity, and output the direct-current electricity; and
a switching circuit configured to receive the direct-current electricity in a case of non-discharge of the battery, receive the direct-current electricity and a discharging current from the battery in a case of discharge of the battery, and perform periodic switching on received current so as to cause an alternating excitation current to flow in the primary winding and generate an induced current in the secondary winding,
wherein the MRI system is configured to perform MRI while receiving the induced current, and
the charge/discharge control circuit is configured to charge the battery with the direct-current electricity.

9. The image diagnosis apparatus according to claim 8, wherein the direct-current power source is configured to output the direct-current electricity with a predetermined voltage when an output current value is equal to or lower than a rated current value, and output the direct-current electricity with a voltage lower than the predetermined voltage when the output current value exceeds the rated current value.

10. The image diagnosis apparatus according to claim 2, further comprising:
a transformer including a plurality of primary windings and a plurality of secondary windings respectively magnetically coupled to the plurality of primary windings;
a direct-current power source configured to receive the external electric power, convert the external electric power into direct-current electricity, and output the direct-current electricity; and
a switching circuit configured to receive the direct-current electricity in a case of non-discharge of the battery, receive the direct-current electricity and a discharging current from the battery in a case of discharge of the battery, and perform periodic switching on received current so as to respectively cause alternating excitation currents to flow in the plurality of primary windings and respectively generate induced currents in the plurality of secondary windings,
wherein the imaging system is configured to perform MRI while respectively receiving the induced currents from the plurality of secondary windings; and
the charge/discharge control circuit is configured to charge the battery with the direct-current electricity.

11. The image diagnosis apparatus according to claim 10, wherein the direct-current power source is configured to output the direct-current electricity with a predetermined voltage when an output current value is equal to or lower than a rated current value, and output the direct-current electricity with a voltage lower than the predetermined voltage when the output current value exceeds the rated current value.

12. The image diagnosis apparatus according to claim 2, further comprising a judging unit configured to provisionally set conditions of an MRI sequence and judge practicability of the MRI sequence before performance of the MRI sequence by calculating the consumed power in a case of performing the MRI sequence based on provisionally set conditions,
wherein the judging unit is configured to set the conditions of the MRI sequence again so as to reduce the consumed power in a case of judging the MRI sequence to be impracticable.

13. The image diagnosis apparatus according to claim 12, further comprising a display device configured to display information of impracticableness, when the MRI sequence is judged to be impracticable by the judging unit.

14. The image diagnosis apparatus according to claim 1, wherein the voltage conversion unit comprises a transformer including a first primary winding, a second primary winding and a secondary winding; and
each winding number of the first primary winding, the second primary winding and the secondary winding is a winding number in accordance with voltages respectively supplied to the plurality of power consuming units.

15. The image diagnosis apparatus according to claim 1, wherein the charge/discharge control circuit is configured to charge the battery during an implementation term of an MRI sequence.

16. The image diagnosis apparatus according to claim 15, wherein the charge/discharge control circuit is configured to control charge and discharge of the battery in such a manner that the battery is charged during an implementation term of an MRI sequence whose consumed power amount is estimated to be equal to or lower than a predetermined value and the battery is not charged during an implementation term of an MRI sequence whose consumed power amount is estimated to exceed the predetermined value.

17. The image diagnosis apparatus according to claim 1, further comprising a computerized tomography structure configured to detect X-rays penetrating the object with a detector, collect projection data based on a detection signal of the detector and reconstruct image data of the object based on the projection data,
wherein the image diagnosis apparatus is configured to comprise an X-ray CT apparatus.

18. A power control method for an image diagnosis apparatus that generates image data of an object by consuming external electric power supplied from an external power source, the apparatus including (A) a magnetic resonance imaging (MRI) system configured to consume external electrical power while generating MRI data of an object, the MRI system including a plurality of power consuming units, each power consuming unit being configured to perform respectively corresponding different imaging operations during an MRI procedure that generates said MRI data, and (B) a battery configured to be charged with the external electric power and to be subsequently discharged while supplying part of the MRI system consumed power, the power control method comprising:
controlling charge and discharge of the battery in such a manner that the consumed power is supplied by the battery and the external power source in a period during which the consumed power is larger than a predetermined power amount and the battery is charged in a period during which the consumed power is smaller than the predetermined power amount; and
converting electric power voltage supplied from at least one of the external power source and the battery, and converting a voltage of electric power supplied from at least one of the external power source and the battery such that arbitrary voltages are respectively supplied to the plurality of power consuming units.

* * * * *